(12) United States Patent
Ochiai et al.

(10) Patent No.: US 8,791,284 B2
(45) Date of Patent: Jul. 29, 2014

(54) ORGANOMETALLIC COMPOUND AND PRODUCTION METHOD THEREOF

(75) Inventors: Takashi Ochiai, Chiba (JP); Haruyuki Makio, Singapore (JP)

(73) Assignee: Mitsui Chemicals, Inc., Tokyo (JP)

( * ) Notice: Subject to any disclaimer, the term of this patent is extended or adjusted under 35 U.S.C. 154(b) by 270 days.

(21) Appl. No.: 13/379,779

(22) PCT Filed: Jun. 30, 2010

(86) PCT No.: PCT/JP2010/061110
§ 371 (c)(1),
(2), (4) Date: Dec. 21, 2011

(87) PCT Pub. No.: WO2011/002000
PCT Pub. Date: Jan. 6, 2011

(65) Prior Publication Data
US 2012/0101289 A1 Apr. 26, 2012

(30) Foreign Application Priority Data

Jul. 1, 2009 (JP) ................................. 2009-156560
Jul. 1, 2009 (JP) ................................. 2009-156561

(51) Int. Cl.
C07F 3/00 (2006.01)
C07F 5/00 (2006.01)
C07F 7/18 (2006.01)
C08F 4/44 (2006.01)
C08F 4/52 (2006.01)

(52) U.S. Cl.
USPC ................... 556/1; 556/9; 556/121; 556/129; 556/178; 526/170; 526/176; 526/177

(58) Field of Classification Search
USPC .......... 556/1, 9, 121, 129, 178; 526/170, 176, 526/177
See application file for complete search history.

(56) References Cited

U.S. PATENT DOCUMENTS

| | | | |
|---|---|---|---|
| 3,084,180 | A | 4/1963 | Gaetano |
| 4,990,640 | A | 2/1991 | Tsutsui et al. |
| 5,321,106 | A | 6/1994 | LaPointe |
| 5,468,707 | A | 11/1995 | Pohl et al. |
| 5,561,092 | A | 10/1996 | Ewen et al. |
| 5,614,457 | A | 3/1997 | Ewen et al. |
| 5,663,249 | A | 9/1997 | Ewen et al. |
| 5,698,761 | A | 12/1997 | Pohl et al. |
| 6,121,395 | A | 9/2000 | Turner |
| 6,444,603 | B1 | 9/2002 | Tohi et al. |
| 6,486,275 | B2 | 11/2002 | Sano et al. |
| 6,838,540 | B2 | 1/2005 | Mitani et al. |
| 6,962,890 | B2 | 11/2005 | Matsukawa et al. |
| 7,566,761 | B2 | 7/2009 | Mitani et al. |
| 7,989,551 | B2 | 8/2011 | Arriola et al. |
| 2009/0118426 | A1 | 5/2009 | Mitani et al. |
| 2011/0028657 | A1 | 2/2011 | Clark et al. |

FOREIGN PATENT DOCUMENTS

| | | |
|---|---|---|
| CN | 1066075 | 11/1992 |
| JP | 62-100506 | 5/1987 |
| JP | 01-501950 A | 7/1989 |
| JP | 01-502036 A | 7/1989 |
| JP | 02-078687 A | 3/1990 |
| JP | 03-179005 A | 8/1991 |
| JP | 03-179006 A | 8/1991 |
| JP | 03-207703 A | 9/1991 |
| JP | 03-207704 A | 9/1991 |
| JP | 07-503660 | 4/1995 |
| JP | 2000-191713 | 7/2000 |

(Continued)

OTHER PUBLICATIONS

Colin Eaborn et al.,Attachment of the Bulky Bidentate Ligand C(SiMe3)2SiMe2CH2CH2Me2Si(Me3Si)2C to K, Zn, Sn, and Yb. Crystal Structures of LnMC(SiMe3)2SiMe2CH2CH2Me2 Si(Me3Si)2CMLn(MLn=K(C6H6)2, K(THF)2, SnCl3, or SnMe2Cl), and CH2SiMe2C(SiMe3)2ZnC(SiMe3)2SiMe2 CH2(THF=Tetrahydrofuran), 1999, vol. 18, No. 12, ISSN:0276-7333, pp. 2342-2348.

Office Action in Japanese Application No. 2011-520941 dated Aug. 27, 2013.

Angewandte Chemie, International Edition in English, 1996, vol. 35, pp. 2-4.

(Continued)

*Primary Examiner* — Porfirio Nazario Gonzalez
(74) *Attorney, Agent, or Firm* — Foley & Lardner LLP

(57) ABSTRACT

It is an object of the present invention to provide a novel organometallic compound functioning usefully as a chain transfer agent and the like in polymerization reaction of a double-bond containing compound. The present invention provides an organometallic compound represented by the following general formula (1) and a production method thereof.

[Chem. 1]

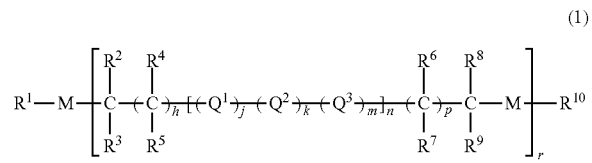

(1)

(in the general formula (1), M is a magnesium atom, a zinc atom, an Al—$R^{11}$ group, or a Ga—$R^{11}$ group; $R^1$ and $R^{10}$ are each independently a hydrocarbon group having 1 to 20 carbon atoms, or $R^1$ and $R^{10}$ may be united with each other to form a divalent connecting group ($R^{101}$) having 4 or more carbon atoms and thus form a ring; $R^2$ to $R^9$ are each independently a hydrogen atom, or a hydrocarbon group having 1 to 20 carbon atoms; $Q^1$ and $Q^3$ are each independently a divalent hydrocarbon group; $Q^2$ is a divalent connecting group containing a linkage by a heteroatom excluding carbon; h, j, k, m, and p are each independently 0 or 1; n is an integer of 0 to 10; and r is an integer of 0 to 1000.

10 Claims, 2 Drawing Sheets

(56) References Cited

FOREIGN PATENT DOCUMENTS

| JP | 2000-239312 | 9/2000 |
|---|---|---|
| JP | 2003-040953 | 2/2003 |
| JP | 2008-533277 | 8/2008 |
| JP | 2013-501093 A | 1/2013 |
| WO | WO-01/55231 A1 | 8/2001 |
| WO | WO-03/014046 A1 | 2/2003 |
| WO | WO-2008/134890 A1 | 11/2008 |

OTHER PUBLICATIONS

Eaborn C., et al. "Attachment of the bulky bidentate Ligand C(SiMe$_3$)$_2$SiMe$_2$CH$_2$CH$_2$Me$_2$Si(Me$_3$Si) C to K, Zn, Sn, and Yb. Crystal Structures of LnMC(SiMe3)2SiMe2CH2 CH2Me2Si(Me3Si)2CMLn (MLn=K(C$_6$H$_6$)$_2$, K(THF)$_2$, SnCl$_3$, or SnMe$_2$Cl) and CH2Sime$_2$C(SiMe)$_2$ZnC(SiMe$_3$)$_2$SiMe$_2$CH2 (THF=Tetrahydrofuran)", Organometallics, 1999, vol. 18, pp. 2342-2348.

Freijee F., et al. "The Synthesis and Structure of Zincacyclopentane, Zincacyclohexane and Zincacycloheptane", Journal of Organometallic Chemistry, 1982, vol. 224, pp. 217-221.

Prasad A., et al. "The preparation of 1,3-dizincapropanes via a boron-zinc transmetallation" Journal of Organometallic Chemistry, 1998, vol. 562, pp. 133-139.

Rozema M., et al. "Preparation of Functionalized Dialkylzinc Reagents via an Iodine-Zinc Exchange Reaction. Highly Enantioselective Synthesis of Functionalized Secondary Alcohols", J. Org. Chem., 1992, vol. 57, pp. 1956-1958.

Bogdanovic, et al. "Organomagnesium inner complexes, Part II. [1] Ethyl(dialkylaminoalkyl)- and Ethyl(4-alkoxybutyl)magnesium compounds", Zeitschrift Fuer Naturforschung, Teil B: Anorganische Chemie, Organische Chemie, 1986, 41B(5). 617-28.

Communication (Supplemental Search Report) in EP appln No. 10794168.4 dated Nov. 15, 2013.

Office Action in CN Appln. No. 201080027611.5 dated Nov. 26, 2013.

ORGANOMETALLIC COMPOUND AND PRODUCTION METHOD THEREOF

TECHNICAL FIELD

The present invention relates to an organometallic compound and a production method thereof, particularly to an organometallic compound containing magnesium, zinc, aluminum or gallium which is useful as a chain transfer agent and an organic synthesis reagent in the polymerization reaction of a double-bond containing compound.

BACKGROUND ART

Organometallic compounds are compounds having a carbon-metal bond (the compounds can include hydride compounds having a hydrogen-metal bond). In general, the carbon-metal bond has high reactivity, and the reactivity is various depending on types of organic groups and metals. Thus, the organometallic compounds have become reaction reagents indispensable to current chemical industry, such as for the use in various organic synthesis reactions. A binuclear organometallic compound having plural carbon-metal bonds in one molecule is expected to have properties such as more various reactivity. Although several cases have been reported about a binuclear organometallic compound having no functional group (Non-Patent Documents 1, 2, and 3), a synthesis method thereof can be hardly said to be an industrial synthesis method. Furthermore, no cases have been reported about a binuclear organometallic compound having a functional group.

On the other hand, it has been well known that in the production of polymers such as polyethylene and polypropylene using a transition metal polymerization catalyst, organometallic compounds such as diethylzinc, trimethylaluminum, triethylaluminum and trioctylaluminum function as a molecular weight regulating agent. Gibson et al. reports that the use of dialkylzinc compounds in olefin polymerization using a certain kind of a transition metal complex can provide an ethylene oligomer one terminal of which is capped with a metal wherein the molecular weight distribution is Poisson-like distribution (Patent Document 1). Here, Poisson distribution is represented by $\chi_p = (x^p e^{-\chi})/p!$, wherein $\chi_p$ is the mole fraction of a polymer obtained after p number of olefins are polymerized, and x is the Poisson coefficient. Because the molecular weight distribution is Poisson-like distribution, the chain transfer from the catalyst to the metal is considered to be reversible, and a chain transfer agent with such nature is referred to as a reversible chain transfer agent. When the reaction of the chain transfer to the organometallic compound is reversible and as fast as chain growth reaction, no unreacted organometallic compound remains and a polymer one terminal of which is capped with a metal can be efficiently obtained.

The reaction of the chain transfer to the organometallic compound in olefin polymerization utilizes a metal exchange reaction, one of the elementary reactions in organometallic chemistry, thereby obtaining a polymer in which formally, the organic group derived from the organometallic compound employed as an molecular weight regulating agent is bonded to one terminal of the olefin polymer, and the metal derived from the organometallic compound is bonded to the other terminal. Modifying a carbon-metal bond at the terminal can lead to the introduction of a functional group into the terminal of the polyolefin.

Furthermore, a both-terminal-functional olefin polymer, having a functional group at both terminals, can be provided with more various properties. Such a both-terminal-functional olefin polymer is synthesized by living polymerization, hydrogenation of metathesis polymers, thermal decomposition of polyolefins, but the synthesis is accompanied by low productivity, low functionalization ratio, low molecular weight, and the like, which limits the application scope.

Among the organometallic compounds, an organozinc compound has been attracting attention for its ability to coexist with functional groups due to its moderate reactivity. Thus, the organozinc compound has been intensively developed as a multi-functionalized organometallic reagent.

The organozinc compound is usually prepared from zinc halides, and organic lithiums or Grignard reagent, the preparation involving by-production of inorganic salts such as lithium halides and magnesium halides. Such by-produced inorganic salts possibly have an influence on reactivity, and thus need to be removed. As a method to remove the by-produced inorganic salts, it has been reported by Charette et al. that a reaction mixture is subjected to centrifugation and a supernatant is used to thereby prepare an organozinc reagent free of by-produced inorganic salts (Patent Document 2), but it must be noted that the centrifugation method under inert atmosphere is difficult to employ on an industrial scale.

A method involving no generation of such inorganic salts has been reported, and effective means is boron-zinc exchange reaction. In this reaction, hydroboronation of borane with a terminal alkyne or a terminal alkene produces an alkyl borane or an alkenyl borane, to which dimethyl or diethyl zinc is acted, and thereby an alkyl or alkenyl zinc compound in which boron has been exchanged with zinc can be obtained. Because the by-product is trialkylborane, which has a low boiling point, the by-product is easy to remove under reduced pressure at a laboratory level, and various cases have been reported about the preparation of various multifunctional alkylzinc compounds (Non-Patent Document 2). In addition, several cases have been reported about the synthesis of cyclic organozinc compounds both terminals of which are metallized by similar methods (Non-Patent Documents 1 and 3). As another method involving no generation of inorganic salts, halogen-metal exchange method can be mentioned. Knochel et al. have reported that an alkyl iodide compound having a functional group is acted to diethylzinc, and then an excessive of diethylzinc and ethyl iodide are removed under reduced pressure, thereby synthesizing an alkyl zinc compound having a functional group (Non-Patent Document 4).

These synthesis methods involving no generation of the inorganic salts, however, require an excessive amount of diethylzinc accompanied by no solvent in order to obtain high reaction yield. In addition, instead of no generation of inorganic salts, alkylboranes, ethyl halides, and the like are by-produced. For this reason, such a method on an industrial scale needs to be performed with advanced reaction control and with advanced safety measures about the use of diethylzinc accompanied by no solvent. Furthermore, it is necessary to provide equipment for removing low boiling point compounds including diethylzinc.

As described above, a number of cases have been reported about methods to synthesize organometallic compounds such as organozinc compounds. However, none of the methods can be said to be efficient in terms of atom economy, because by-products are generated such as inorganic salts, alkylboranes and alkyl halides, and there has been no method provided which are employable and efficient on an industrial basis. Therefore, a more practical production method has been desired.

CITATION LIST

Patent Documents

Patent Document 1: WO-2003-014046 pamphlet
Patent Document 2: WO-2008-134890 pamphlet
Non-Patent Document 1: J. Organomet. Chem. 1998, 562, 133-139
Non-Patent Document 2: Angew. Chem., Int. Ed. Eng. 1996, 35. 2-4
Non-Patent Document 3: J. Organomet. Chem. 1982, 224, 217-221
Non-Patent Document 4: J. Org. Chem., 1992, 57, 1956-1958

SUMMARY OF THE INVENTION

Problem to be Solved by the Invention

It is an object of the present invention to provide a novel organometallic compound functioning usefully as a chain transfer agent and the like in polymerization reaction of a double-bond containing compound, and being capable of producing a useful both-terminal-functional olefin polymer. It is another object of the present invention to provide a method for efficiently producing such a novel organometallic compound.

Means for Solving the Problem

An organometallic compound (1) of the present invention has a structure represented by the following general formula (1).

[Chem. 1]

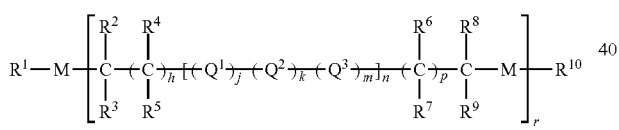

In the general formula (1), M is a magnesium atom, a zinc atom, an Al—$R^{11}$ group, or a Ga—$R^{11}$ group, provided that $R^{11}$ is a hydrogen atom, a hydrocarbon group, a halogen atom, a silicon-containing group, or an oxygen-containing group; $R^1$ and $R^{10}$ are each independently a hydrocarbon group having 1 to 20 carbon atoms, or $R^1$ and $R^{10}$ may be united with each other to form a divalent connecting group ($R^{101}$) having 4 or more carbon atoms and optionally containing a heteroatom excluding carbon and hydrogen and thus form a ring; $R^2$ to $R^9$ are each independently a hydrogen atom, or a hydrocarbon group having 1 to 20 carbon atoms; $Q^1$ and $Q^3$ are each independently a divalent hydrocarbon group; $Q^2$ is a divalent connecting group containing a linkage by a heteroatom excluding carbon; h, j, k, m, and p are each independently 0 or 1; n is an integer of 0 to 10; and r is an integer of 0 to 10000, provided that:

$R^1$ to $R^{11}$ may be a group formed by substituting a part of the hydrogen atoms of the hydrocarbon group with a substituent containing a heteroatom excluding carbon and hydrogen; $Q^1$ and $Q^3$ may be a group formed by substituting a part of the hydrogen atoms of the divalent hydrocarbon group with a substituent containing a heteroatom excluding carbon and hydrogen;

when h is 0, at least one of $R^2$ and $R^3$ is a hydrocarbon group having 2 to 20 carbon atoms; when h is 1, at least one of $R^4$ and $R^5$ is a hydrocarbon group having 1 to 20 carbon atoms; when p is 0, at least one of $R^8$ and $R^9$ is a hydrocarbon group having 2 to 20 carbon atoms; when p is 1, at least one of $R^6$ and $R^7$ is a hydrocarbon group having 1 to 20 carbon atoms;

when n is 2 or more, plural $Q^1$, $Q^2$, $Q^3$, j, k, and m may be individually the same as or different from one another;

when r is 0, $R^1$ and $R^{10}$ are united with each other to form a divalent connecting group ($R^{101}$) having 4 or more carbon atoms and optionally containing a heteroatom excluding carbon and hydrogen and thus form a ring;

when r is 1 or more, plural M may be the same as or different from one another; when plural $R^{11}$ are present, they may be the same as or different from one another; and when r is 2 or more, plural $Q^1$, $Q^2$, $Q^3$, h, j, k, m, n, p, and $R^2$ to $R^9$ may be individually the same as or different from one another.

The organometallic compound (1) of the present invention includes those represented by the following general formulae (2), (3a), (3b), (3c), and (4)

[Chem. 2]

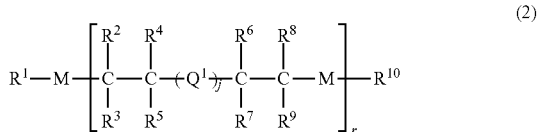

[Chem. 3]

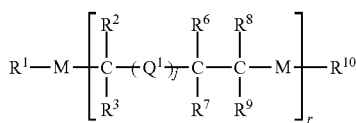

[Chem. 4]

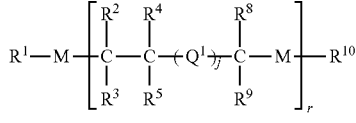

[Chem. 5]

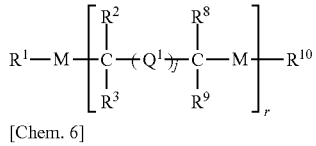

[Chem. 6]

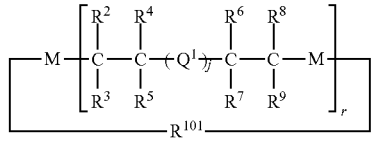

In the general formulae (2), (3a), (3b), (3c), and (4), M, $R^1$ to $R^{10}$, $Q^1$, j, and r are each defined in the same way as in the general formula (1) of claim 1; and $R^{101}$ is a divalent connecting group having 4 or more carbon atoms and optionally containing a heteroatom excluding carbon and hydrogen.

In the organometallic compound (1) of the present invention, M is preferably an Al—$R^{11}$ group or a zinc atom.

An organometallic compound (5) of the present invention is represented by the following general formula (5).

[Chem. 7]

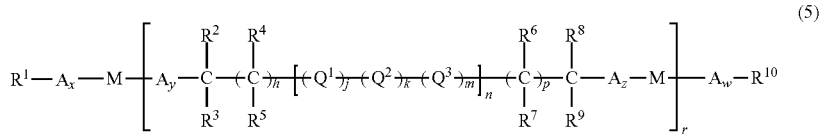

In the general formula (5), A is a unit derived from a linear or branched α-olefin having 2 to 30 carbon atoms, a cyclic olefin, a diene, a polyene, or an aromatic vinyl compound; x, y, z, and w are each an integer of 1 or more; and x+y+z+w=8 to 100000. M, $Q^1$, $Q^2$, $Q^3$, h, j, k, m, n, p, and $R^1$ to $R^{10}$ are defined in the same manner as in the general formula (1).

A method for producing the organometallic compound of the present invention is characterized in that in the presence of a transition metal compound (A) represented by the following general formula (A), a diene compound (B) represented by the following genera formula (B) is reacted with an organometallic compound (C) represented by the following general formula (C) to thereby obtain the above organometallic compound (1).

[Chem. 8]

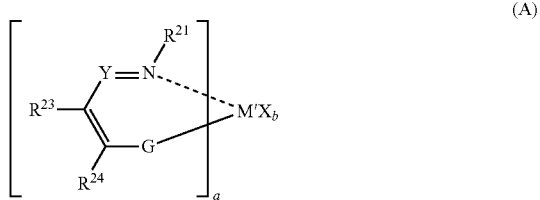

In the general formula (A), M' is a transition metal atom selected from Groups 3 to 11 of the periodic table of the elements (Group 3 includes a lanthanoid and an actinoid); a is an integer of 1 to 3, which is the number of ligands coordinated with the transition metal atom M'; X is an atom or a group selected from the group consisting of a hydrogen atom, a halogen atom, an oxygen atom, a hydrocarbon group, a silicon-containing group, germanium-containing group, a tin-containing group, a boron-containing group, an aluminum-containing group, a phosphorus-containing group, an oxygen-containing group, a sulfur-containing group, a nitrogen-containing group, a halogen-containing group, and a heterocyclic compound residue; b is an integer of 0 to 3, which is the number of X; when b is 2 or 3, X may be the same as or different from one another, and plural X may be united with one another to form a ring; Y is a nitrogen atom, or a carbon atom having a substituent $R^{22}$; G is an oxygen atom, a sulfur atom, a selenium atom, or a nitrogen atom having a substituent $R^{25}$; $R^{21}$ to $R^{25}$ may be the same as or different from one another, and are an atom or a group selected from the group consisting of a hydrocarbon group, a halogen atom, a hydrogen atom, a hydrocarbon-substituted silyl group, an oxygen-containing group, a nitrogen-containing group, a sulfur-containing group, a boron-containing group, an aluminum-containing group, a phosphorus-containing group, a halogen-containing group, a heterocyclic compound residue, a silicon-containing group, a germanium-containing group, and a tin-containing group; two or more of $R^{22}$ to $R^{25}$ may be united with one another to form a ring; and when a is 2 or 3, $R^{21}$s, $R^{22}$s, $R^{23}$s, $R^{24}$s, and $R^{25}$s may be individually the same as or different from one another, and one group of $R^{22}$-$R^{25}$ contained in any one of the ligands and one group of $R^{22}$-$R^{25}$ contained in another ligand may be united.

[Chem. 9]

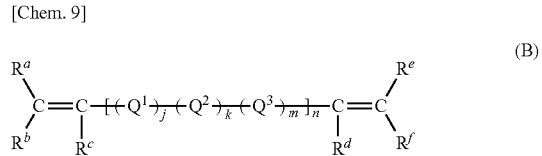

In the general formula (B), $R^a$ to $R^f$ are each independently a hydrogen atom, or a hydrocarbon group having 1 to 20 carbon atoms, and may be a group formed by substituting a part of the hydrogen atoms of the hydrocarbon group with a substituent containing a heteroatom excluding carbon and hydrogen; and $Q^1$, $Q^2$, $Q^3$, j, k, m, and n are each defined in the same manner as in the general formula (1).

[Chem. 10]

R-M-R  (C)

In the general formula (C), M is defined in the same manner as in the general formula (1); two R are each independently a hydrocarbon group having 1 to 20 carbon atoms, and may be a group formed by substituting a part of the hydrogen atoms of the hydrocarbon group with a substituent containing a heteroatom excluding carbon and hydrogen.

The transition metal compound (A) employed in the production method of the present invention is preferably a transition metal compound (A1) represented by the following general formula (A1).

[Chem. 11]

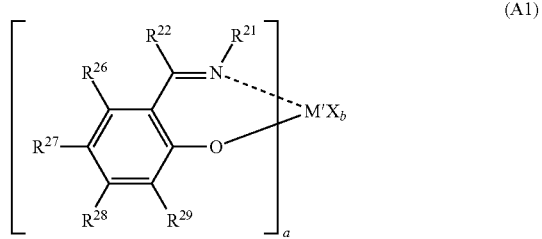

In the general formula (A1), M', a, X, b, $R^{21}$, and $R^{22}$ are each defined in the same manner as in the general formula (A) of claim 1; $R^{26}$ to $R^{29}$ may be the same as or different from one another, and are an atom or a group selected from the group consisting of a hydrogen atom, a hydrocarbon group, a halogen atom, a hydrocarbon-substituted silyl group, an oxygen-containing group, a nitrogen-containing group, a sulfur-containing group, a boron-containing group, an aluminum-containing group, a phosphorus-containing group, a halogen-containing group, a heterocyclic compound residue, a silicon-containing group, a germanium-containing group, and a tin-containing group, and of these, two or more may be united with one another to form a ring; and when a is 2 or 3, $R^{21}$s, $R^{22}$s, $R^{26}$s, $R^{27}$s, $R^{28}$s and $R^{29}$s may be individually the same as or different from one another, and one group of $R^{22}$ and $R^{26}$-$R^{29}$ contained in any one of the ligands and one group of $R^{22}$ and $R^{26}$-$R^{29}$ contained in another ligand may be united.

M in the organometallic compound (C) is preferably an Al—$R^{11}$ group or a zinc atom.

Furthermore, the production method of the present invention preferably employs a co-catalyst and a carrier.

In the production method of the organometallic compound of the present invention, the production method of the organometallic compound (5) is characterized in that the organometallic compound (1) is reacted with linear or branched α-olefins having 2 to 30 carbon atoms, cyclic olefins, dienes, polyenes, or aromatic vinyl compounds.

The production method of a both-terminal-functional polymer of the present invention is characterized by performing functional group conversion reaction at carbon-metal bonds of the organometallic compound (5).

Effects of the Invention

The novel organometallic compound of the present invention is useful as a chain transfer agent in polymerization reaction of a double-bond containing compound, and can be used particularly as a reversible chain transfer agent in polymerization reaction, and is capable of producing a polymer having a carbon-metal bond at both terminals. By performing functional group conversion by known methods at the carbon-metal bonds in the polymer having a carbon-metal bond at both terminals, a both-terminal-functional polymer can be produced.

According to the production method of the present invention, it is possible to efficiently produce a novel organometallic compound which is useful as a chain transfer agent in polymerization reaction of a double-bond containing compound, and can be used particularly as a reversible chain transfer agent in polymerization reaction and also as an organic synthesis reagent, a polymer material, or a precursor thereof. Starting from an organometallic compound obtainable by the method of the present invention, a polymer having a carbon-metal bond at both terminals can be produced. Furthermore, by performing functional group conversion at the carbon-metal bonds by known methods, a both-terminal-functional polymer can be produced.

EMBODIMENTS FOR CARRYING OUT THE INVENTION

Organometallic Compound (1)

Figure 1:
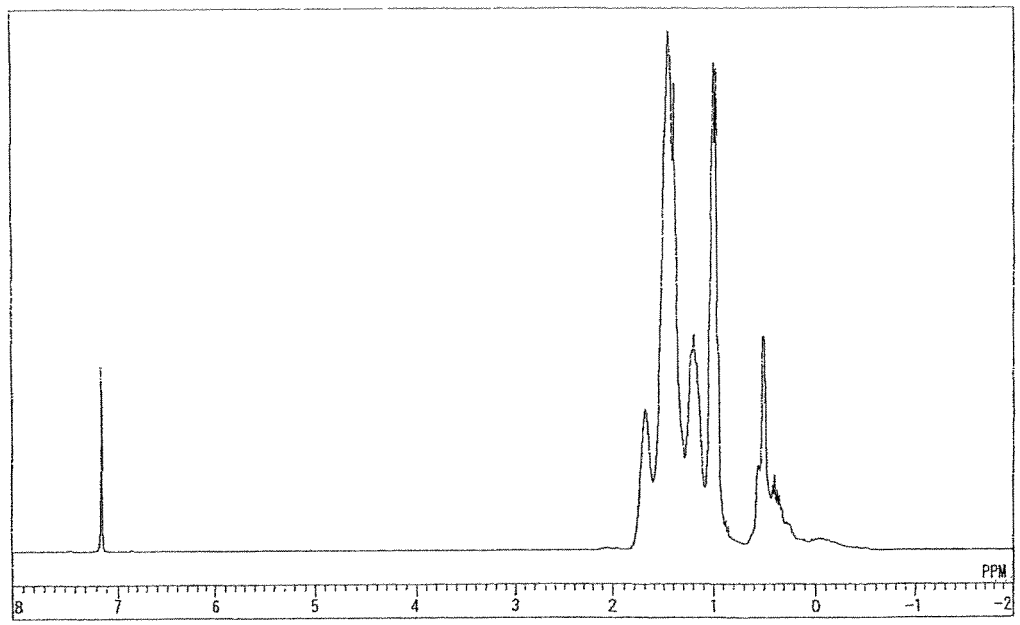
FIG. 1 is a $^1$H-NMR spectrum of a compound X-1 synthesized in Example 1.

The organometallic compound of the present invention has a structure represented by the following general formula (1).

[Chem. 12]

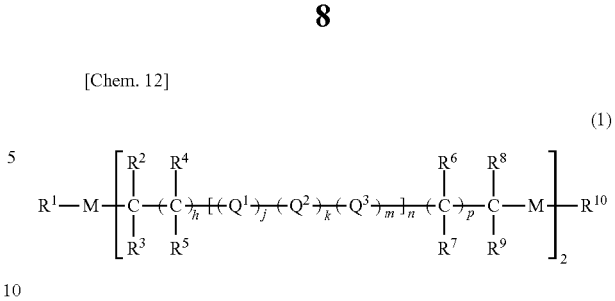

In the general formula (1), M is a magnesium atom, a zinc atom, an Al—$R^{11}$ group, or a Ga—$R^{11}$ group; when r is 1 or more, plural M may be the same as or different from one another; M is preferably a zinc atom, or an Al—$R^{11}$ group; and all of the M are preferably zinc atoms.

$R^{11}$ is a hydrogen atom, a hydrocarbon group, a halogen atom, a silicon-containing group, or an oxygen-containing group.

Examples of the hydrocarbon group include alkyl groups having 1 to 20 carbon atoms, aryl groups, and aryl alkyl groups. Specific examples thereof include methyl group, ethyl group, propyl group, isopropyl group, n-butyl group, isobutyl group, sec-butyl group, tert-butyl group, pentyl group, neopentyl group, hexyl group, octyl group, decyl group, cyclohexyl group, phenyl group, tolyl group, naphthyl group, benzyl group, and 2-phenylethyl group. $R^{11}$ may be a group formed by substituting a part of the hydrogen atoms of the hydrocarbon group with a substituent containing a heteroatom excluding carbon and hydrogen. As used in the present invention, the "heteroatom" is referred to as including all atoms except for carbon and hydrogen. Examples of the group formed by substituting the hydrocarbon group with the substituent containing a heteroatom include methoxymethyl group, ethoxymethyl group, methoxyethyl group, ethoxyethyl group, aminomethyl group, aminoethyl group, dimethyl aminomethyl group, diethyl aminomethyl group, and diphenyl aminomethyl group; and silicon-containing hydrocarbon groups, such as trimethyl silylmethyl group, triethyl silylmethyl group, trimethoxy silylmethyl group, triisopropyl silylmethyl group, triphenyl silylmethyl group, tert-butyldimethyl silylmethyl group, trimethyl silylethyl group, triethyl silylethyl group, trimethoxy silylethyl group, triisopropyl silylethyl group, triphenyl silylethyl group, and tert-butyldimethyl silylethyl group.

Examples of the halogen atom include fluorine, chlorine, bromine, and iodine.

The silicon-containing group is a group containing a silicon atom and having a bond at the silicon atom, with examples thereof including trimethyl silyl group, trimethoxy silyl group, triethyl silyl group, triisopropyl silyl group, and tert-butyldimethyl silyl group.

Examples of the oxygen-containing group include alkoxy groups such as methoxy group, ethoxy group, propoxy group, and butoxy group, ketones such as methyl carbonyl group, ethyl carbonyl group, propyl carbonyl group, isopropyl carbonyl group, n-butyl carbonyl group, sec-butyl carbonyl group, tert-butyl carbonyl group, isobutyl carbonyl group, methoxy carbonyl group, ethoxy carbonyl group, propoxy carbonyl group, isopropoxy carbonyl group, n-butoxy carbonyl group, sec-butoxy carbonyl group, tert-butoxy carbonyl group, and isobutoxy carbonyl group, ester group, and hydroxyl group.

Of the above atom and groups, as $R^{11}$, preferable are methyl group, ethyl group, propyl group, isopropyl group, n-butyl group, isobutyl group, sec-butyl group, tert-butyl group, pentyl group, hexyl group, octyl group, phenyl group, benzyl group, trimethyl silyl group, trimethyl silyl methyl group, triethyl silyl methyl group, and triisopropyl silyl methyl group; and more preferable are methyl group, ethyl group, isopropyl group, isobutyl group, hexyl group, phenyl group, trimethyl silyl methyl group, and benzyl group.

$R^1$ and $R^{10}$ are each independently a hydrocarbon group having 1 to 20 carbon atoms, and may be a group formed by substituting a part of the hydrogen atoms of the hydrocarbon group with a substituent containing a heteroatom excluding carbon and hydrogen. Examples of the hydrocarbon group having 1 to 20 carbon atoms can be mentioned as the examples of the hydrocarbon group referred to as $R^{11}$. $R^1$ and $R^{10}$ are preferably alkyl groups, aryl groups, and aryl alkyl groups, having 1 to 20 carbon atoms, with preferable examples thereof including methyl group, ethyl group, propyl group, isopropyl group, n-butyl group, isobutyl group, sec-butyl group, tert-butyl group, neopentyl group, phenyl group, benzyl group, and trimethyl silyl methyl group.

$R^1$ and $R^{10}$ may be united with each other to become $R^{101}$, thereby forming a ring as a whole in such a manner as represented in the following general formula (1').

[Chem. 13]

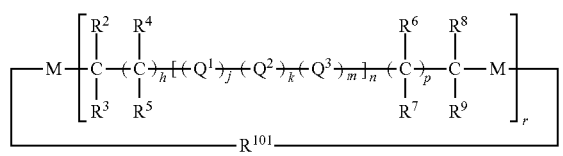
(1')

In this case, $R^{101}$ is a divalent connecting group having 4 or more carbon atoms and optionally containing a heteroatom excluding carbon and hydrogen. $R^{101}$ is typically represented by the following general formula (a) in which case an organometallic compound as a whole is represented by the following general formula (1")

[Chem. 14]

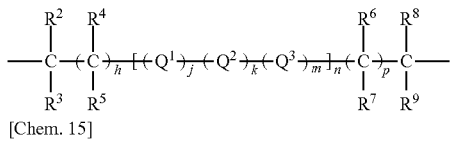
(a)

[Chem. 15]

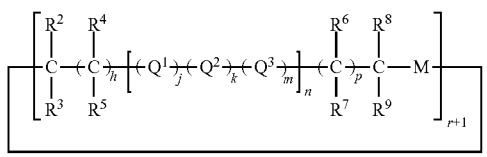
(1")

In the general formulae (a) and (1"), M, $R^2$ to $R^9$, $Q^1$, $Q^2$, $Q^3$, h, j, k, m, n, p, and r are each defined in the same manner as in the general formula (1).

$R^2$ to $R^9$ are each independently a hydrogen atom, or a hydrocarbon group having 1 to 20 carbon atoms, and may be a group formed by substituting a part of the hydrogen atoms of the hydrocarbon group with a substituent containing a heteroatom excluding carbon and hydrogen. Examples of the hydrocarbon group having 1 to 20 carbon atoms can be mentioned as the examples of the hydrocarbon group referred to as $R^{11}$.

Of these groups, $R^2$, $R^3$, $R^8$, and $R^9$ are preferably a hydrogen atom, methyl group, ethyl group, propyl group, isopropyl group, n-butyl group, isobutyl group, sec-butyl group, n-pentyl group, hexyl group, heptyl group, octyl group, nonyl group, decyl group, and benzyl group, and more preferably, a hydrogen atom, methyl group, ethyl group, propyl group, isopropyl group, and benzyl group.

$R^4$, $R^5$, $R^6$, and $R^7$ are preferably a hydrogen atom, methyl group, ethyl group, propyl group, isopropyl group, n-butyl group, isobutyl group, sec-butyl group, tert-butyl group, n-pentyl group, hexyl group, heptyl group, octyl group, nonyl group, decyl group, and phenyl group, and more preferably, a hydrogen atom, methyl group, ethyl group, propyl group, isopropyl group, and phenyl group.

h and p are each independently 0 or 1, provided that when h is 0, at least one of $R^2$ and $R^3$ is a hydrocarbon group having 2 to 20 carbon atoms, when h is 1, at least one of $R^4$ and $R^5$ is a hydrocarbon group having 1 to 20 carbon atoms, when p is 0, at least one of $R^8$ and $R^9$ is a hydrocarbon group having 2 to 20 carbon atoms, and when p is 1, at least one of $R^6$ and $R^7$ is a hydrocarbon group having 1 to 20 carbon atoms. The characteristics of the structures of $R^2$ to $R^9$ are derived from the method for producing the organometallic compound (1) of the present invention. This will be described later.

$Q^1$ and $Q^3$ are each independently a divalent hydrocarbon group, and may be a group formed by substituting a part of the hydrogen atoms of the hydrocarbon group with a substituent containing a heteroatom excluding carbon and hydrogen. Examples of the divalent hydrocarbon group include saturated hydrocarbon groups having 1 to 20 carbon atoms, such as —$CH_2$—, —$(CH_2)_2$—, —$(CH_2)_3$—, and —$(CH_2)_4$—; unsaturated hydrocarbon groups having 1 to 20 carbon atoms, such as —CH═CH—, —CH═CH—$CH_2$—, —$CH_2$—CH═CH—, —$CH_2$—CH═CH—$CH_2$—, —C≡C—, and —C≡C—$CH_2$—; cyclic saturated hydrocarbon groups, such as cyclopentylidene, cyclopentylene, cyclohexylidene, and cyclohexylene; aromatic hydrocarbon groups such as groups having such an aromatic ring as represented by the following formulae:

[Chem. 16]

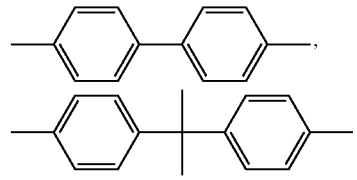

and residues of cyclic hydrocarbons having 6 to 20 carbon atoms, e.g., benzene, naphthalene, and anthracene, and combinations thereof, and may be a group formed by substituting a part of the hydrogen atoms of the hydrocarbon groups with a hydrocarbon group; a halogen atom such as fluorine, chlorine, and bromine; and a group containing a heteroatom such as oxygen, sulfur, nitrogen, phosphorus, silicon, germanium, tin, and boron.

$Q^2$ is a divalent connecting group containing a linkage by a heteroatom excluding carbon. Examples of the heteroatom include oxygen, sulfur, nitrogen, phosphorus, silicon, germanium, tin, and boron. Examples of the divalent connecting group containing a linkage by such a heteroatom include —O—, —O—$CH_2$—, —O—$CH_2$—O—, —(O—$CH_2$)$_n$—O—, —O—$(CH_2)_2$—O—, —(O—$(CH_2)_2)_n$—O—, —$CH_2$—O—$CH_2$—, —O—$SiH_2$—, —O—$SiH_2$—O—, —S—, —SO$_2$—, —(O—SiH$_2$)$_n$—O—, —O—(SiH$_2$)$_n$—, —NH—CO—, —N=CH—, —CO$_2$—, —NH—, —PH—, —SiH$_2$—, —GeH—, —SnH$_2$—, and —BH—. A part of the hydrogen atoms of these connecting groups may be substituted with a hydrocarbon group, a halogen atom such as fluorine, chlorine, and bromine, and a group containing a heteroatom such as oxygen, sulfur, nitrogen, phosphorus, silicon, germanium, tin, and boron.

j, k, and m are each independently 0 or 1. n is an integer of 0 to 10. r is an integer of 0 to 10000. r is preferably an integer of 2 to 10000, more preferably an integer of 5 to 1000, still more preferably an integer of 20 to 500.

When n is 2 or more, plural $Q^1$, $Q^2$, $Q^3$, j, k, and m may be individually the same as or different from one another. When r is 0, $R^1$ and $R^{10}$ are united with each other to form a divalent connecting group ($R^{101}$) having 4 or more carbon atoms and optionally containing a heteroatom excluding carbon and hydrogen and thus form a ring. When r is 1 or more, plural M may be the same as or different from one another. When plural $R^{11}$ are present, they may be the same as or different from one another. When r is 2 or more, plural $Q^1$, $Q^2$, $Q^3$, h, j, k, m, n, p, and $R^2$ to $R^9$ may be individually the same as or different from one another.

Examples of the organometallic compound (1) represented by the general formula (1) include those represented by the following general formulae (2), (3a), (3b), (3c), and (4).

[Chem. 17]

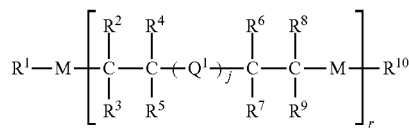

(2)

[Chem. 18]

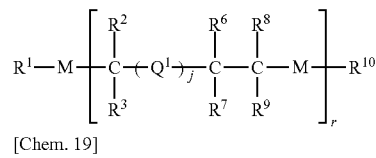

(3a)

[Chem. 19]

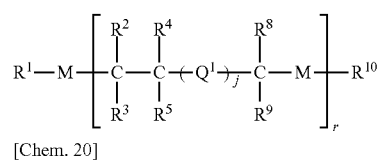

(3b)

[Chem. 20]

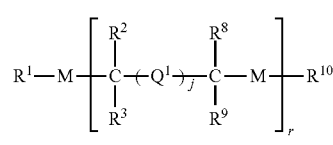

(3c)

[Chem. 21]

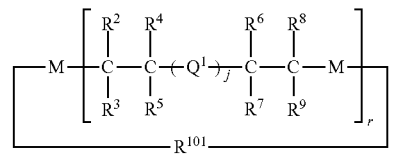

(4)

Specific examples of the organometallic compound of the present invention represented by the general formula (1) include compounds represented by the following formulae. In the following formulae, Me denotes methyl group, Et denotes ethyl group, Pr denotes propyl group, Bu denotes butyl group, Ph denotes phenyl group, and TMS denotes trimethyl silyl group.

[Chem. 22]

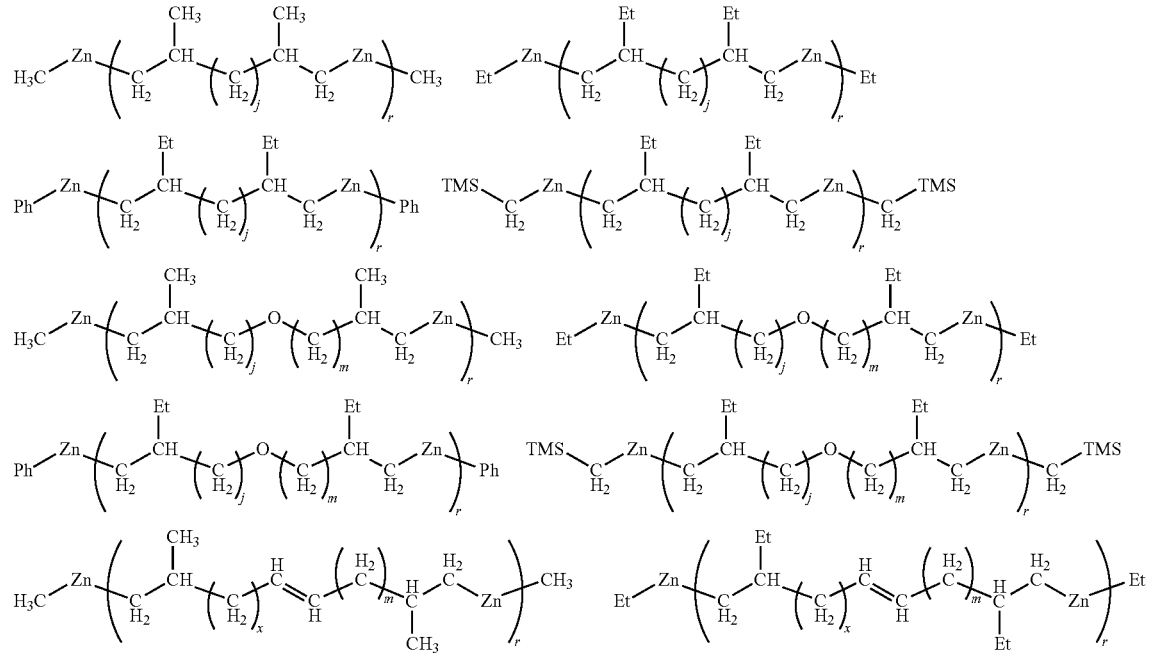

-continued
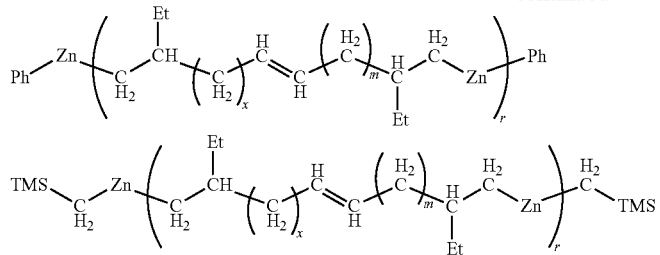
[Chem. 23]
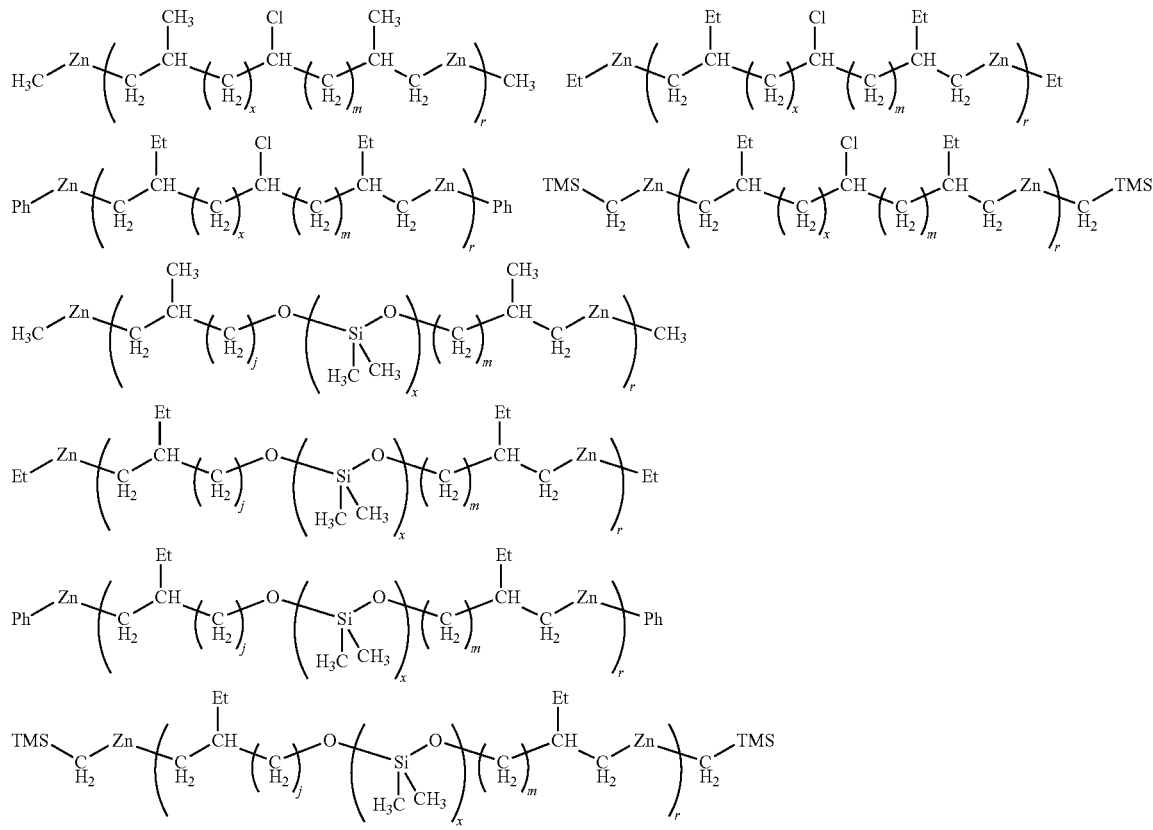
[Chem. 24]
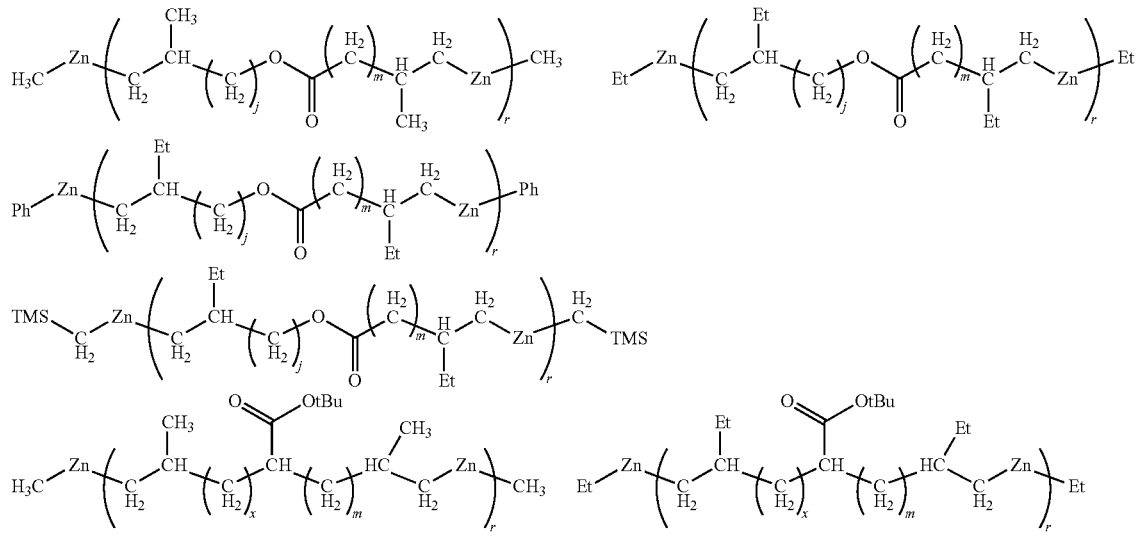

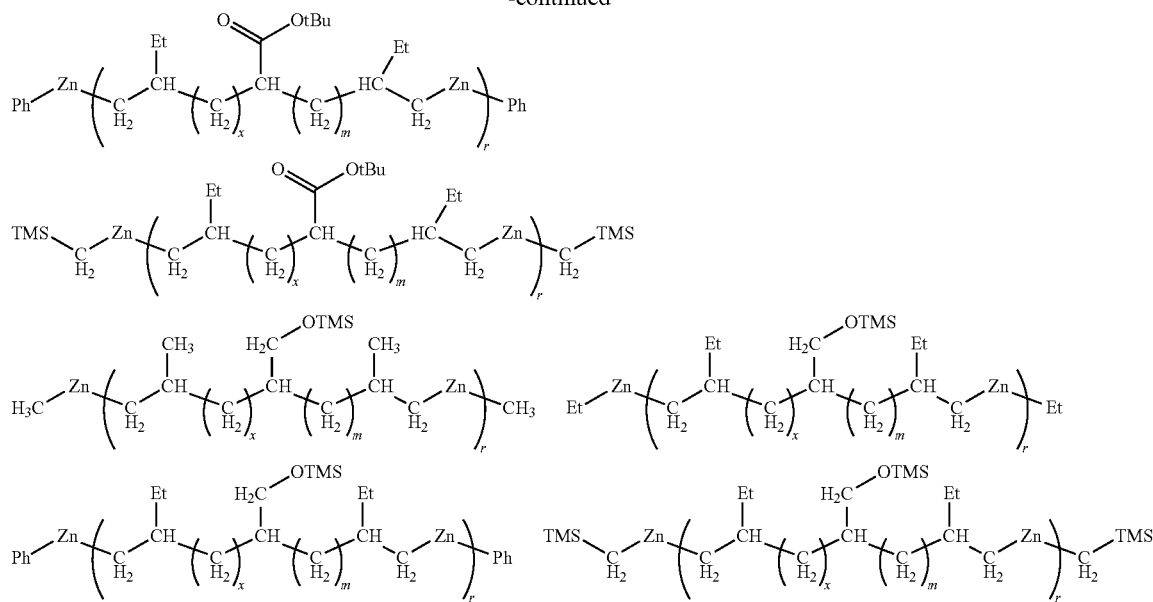
[Chem. 25]
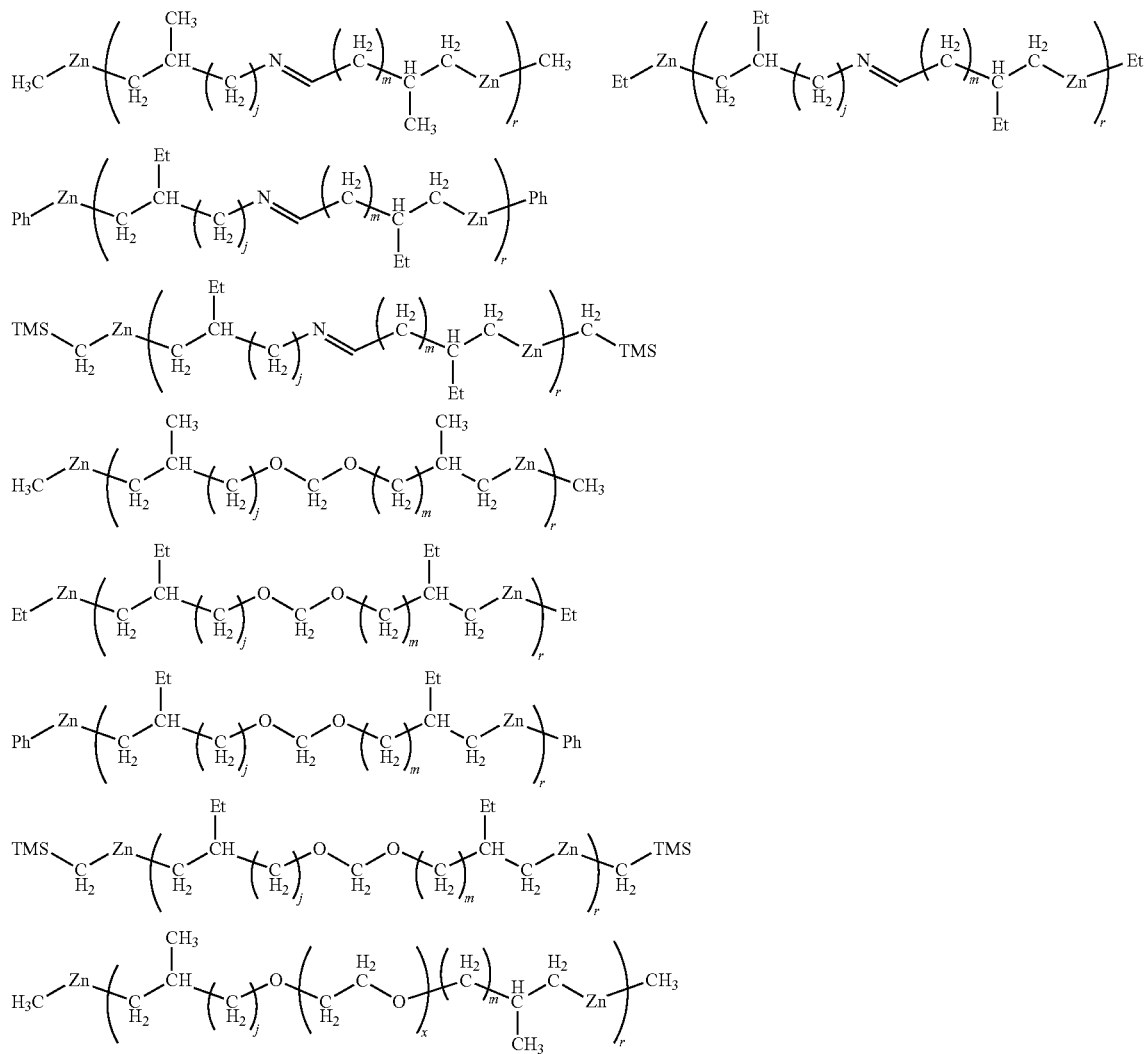

-continued
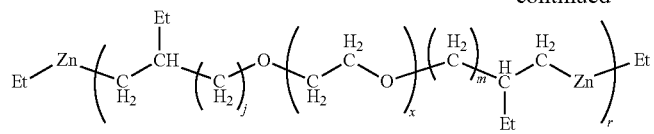
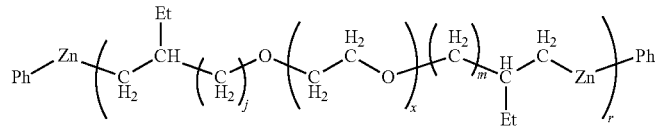
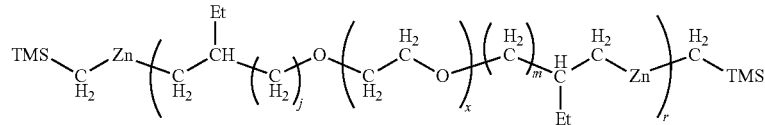
[Chem. 26]
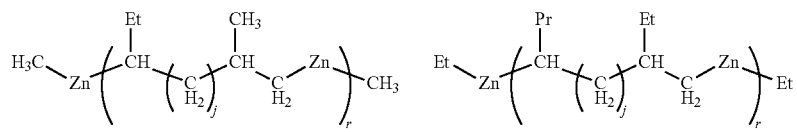
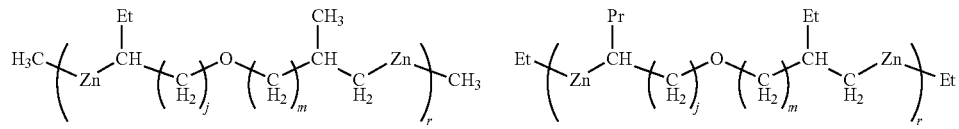
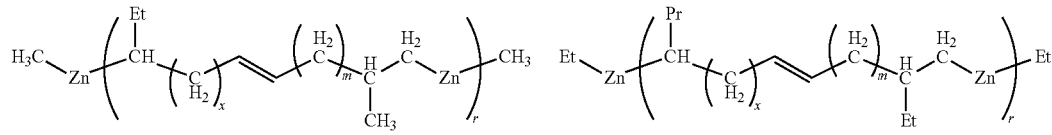
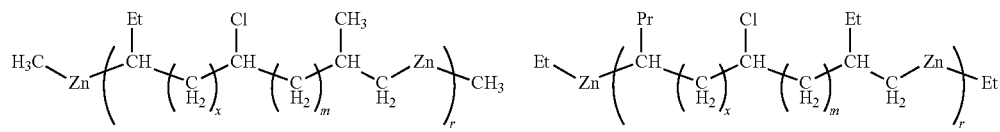
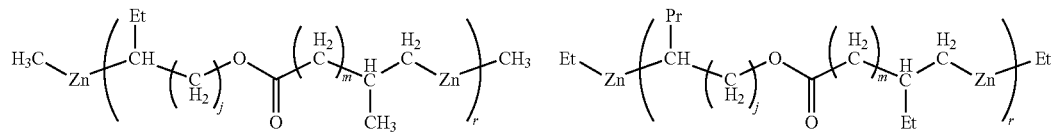
[Chem. 27]
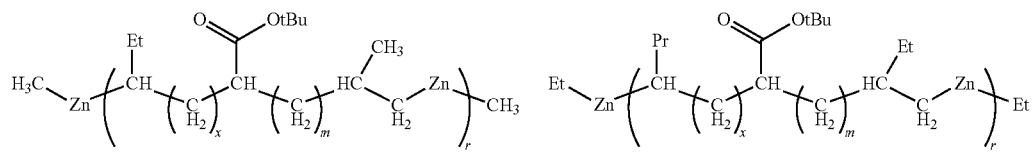
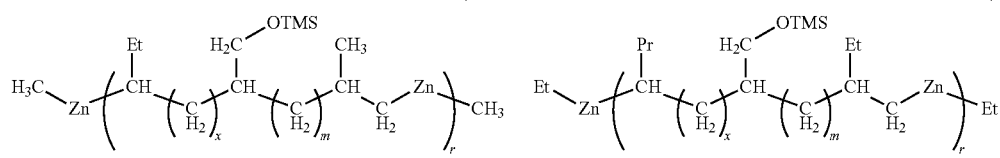
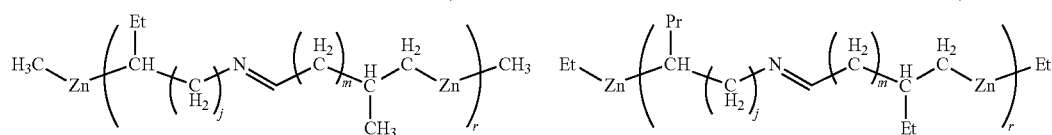
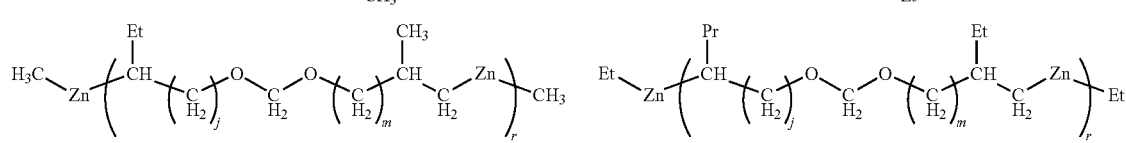

-continued

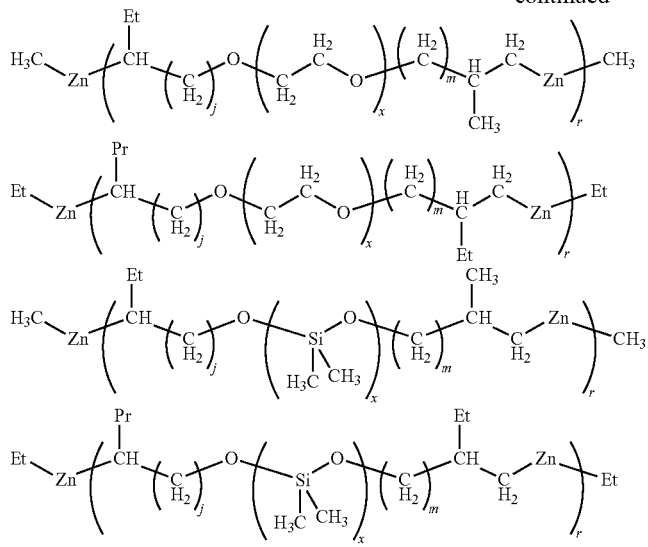

[Method for Producing Organometallic Compound (1)]

The organometallic compound (1) of the present invention can be produced by reactions such as a reaction between a halogenated zinc and a corresponding organolithium or Grignard reagent, or a boron zinc exchange reaction between a corresponding boron compound and an alkylzinc, but is preferably produced by a method using a transition metal compound (A), described later, as a catalyst. Hereinafter, the method for producing the organometallic compound (1) of the present invention using the transition metal compound (A) as a catalyst is described in detail.

The method for producing the organometallic compound of the present invention is characterized in that in the presence of the transition metal compound (A) represented by the following general formula, a diene compound (3) represented by the following general formula is reacted with an organometallic compound (C) represented by the following general formula, to thereby obtain the organometallic compound (1) represented by the general formula (1).

Transition Metal Compound (A)

The transition metal compound (A) employed in the method for producing the organometallic compound (1) of the present invention is represented by the following formula (A).

[Chem. 28]

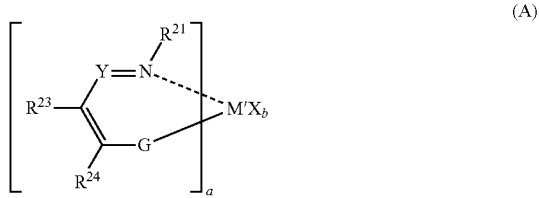

In the general formula (A), M' is a transition metal atom selected from Groups 3 to 11 of the periodic table of the elements (Group 3 includes a lanthanoid and an actinoid), preferably a transition metal atom of Group 4 or 5, more preferably a transition metal atom of Group 4, and specific examples thereof include titanium, zirconium, and hafnium, and a particularly preferable is zirconium.

Here, N . . . M' generally denotes coordination, but in the present invention, coordination may be take place or may not take place.

a is an integer of 1 to 3, which is the number of a ligand coordinated with the transition metal atom M'. When a is 2 or 3, ligands may be the same as or different from one another, and plural ligands may be united with one another via one or more bridging groups selected from the group consisting of a hydrocarbon group, a silicon-containing group, a germanium-containing group, a tin-containing group, a boron-containing group, an aluminum-containing group, a phosphorus-containing group, an oxygen-containing group, a sulfur-containing group, and a nitrogen-containing group. a is preferably 1 or 2, more preferably 2.

X is an atom or a group selected from the group consisting of a hydrogen atom, a halogen atom, an oxygen atom, a hydrocarbon group, licon-containing group, a germanium-containing group, a tin-containing group, a boron-containing group, an aluminum-containing group, a phosphorus-containing group, an oxygen-containing group, a sulfur-containing group, a nitrogen-containing group, a halogen containing group, and a hetrocyclic compound residue. b is an integer of 0 to 3, which is the number of X. When b is 2 or 3, X may be the same as or different from one another, and plural X may be united with one another to form a ring.

Examples of the halogen atom include a fluorine atom, a chlorine atom, a bromine atom, and an iodine atom.

Examples of the hydrocarbon group include alkyl groups such as methyl, ethyl, propyl, butyl, hexyl, octyl, nonyl, dodecyl, eicosyl; cycloalkyl groups having 3 to 30 carbon atoms such as cyclopentyl, cyclohexyl, norbonyl, and adamantyl; alkenyl groups such as vinyl, propenyl, and cyclohexenyl; aryl alkyl groups such as benzyl, phenyl ethyl, and phenyl propyl; and aryl groups such as phenyl, tolyl, dimethyl phenyl, trimethyl phenyl, ethyl phenyl, propyl phenyl, biphenyl, naphthyl, methyl naphthyl, anthryl, and phenanthryl.

The silicon-containing group is a group which has 1 to 5 silicon atoms in a residue and which excludes a heterocyclic compound residue. Specific examples thereof include hydrocarbon-substituted silyl groups such as phenyl silyl, diphenyl silyl, trimethyl silyl, triethyl silyl, tripropyl silyl, tricyclohexyl silyl, triphenyl silyl, methyl diphenyl silyl, tritolyl silyl, and trinaphthyl silyl; hydrocarbon-substituted silyl ether groups such as trimethyl silyl ether; silicon-substituted alkyl groups such as trimethyl silyl methyl; and silicon-substituted aryl groups such as trimethyl silyl phenyl. When the silicon-containing group contains a carbon atom, the number of the carbon atom is 1 to 30, preferably 1 to 20.

The germanium-containing group is a group which has a germanium atom and which excludes a heterocyclic compound residue. Examples thereof include those in which the silicon of the above silicon-containing group is substituted with germanium. The tin-containing group is a group having a tin atom excluding a heterocyclic compound residue. Examples thereof include those in which the silicon of the above silicon-containing group is substituted with tin.

The boron-containing group is a group which has 1 to 5 boron atoms in a group and which excludes a heterocyclic compound residue. Specific examples thereof include $ER_4$ (R is a hydrogen atom, an alkyl group, an aryl group optionally having a substituent, a halogen atom, or the like).

The aluminum-containing group is a group which has 1 to 5 aluminum atom in a group and which excludes a heterocyclic compound residue. Specific examples thereof include $AlR_4$ (R is a hydrogen atom, an alkyl group, an aryl group optionally having a substituent, a halogen atom, or the like).

The phosphorus-containing group is a group which has 1 to 5 phosphorus atoms in a group and which excludes a heterocyclic compound residue. Specific examples thereof include trialkyl phosphine groups such as trimethylphosphine, tributyl phosphine, and tricyclohexyl phosphine; triaryl phosphine groups such as triphenyl phosphine, and tritolyl phosphine; phosphite groups (phosphide groups) such as methyl phosphite, ethyl phosphite, and phenyl phosphite; phosphonic group; and phosphinic acid group.

The oxygen-containing group is a group which has 1 to 5 oxygen atoms in a group and which excludes a heterocyclic compound residue. Specific examples thereof include hydroxyl group; alkoxy groups such as methoxy, ethoxy, propoxy, and butoxy; aryloxy groups such as phenoxy, methyl phenoxy, dimethyl phenoxy, and naphthoxy; aryl alkoxy groups such as phenyl methoxy, and phenyl ethoxy; acetoxy group; and carbonyl group. When the oxygen-containing group contains a carbon atom, the number of the carbon atom is 1 to 30, preferably 1 to 20.

The sulfur-containing group is a group which has 1 to 5 sulfur atoms in a group and which excludes a heterocyclic compound residue. Specific examples thereof include sulfonate groups such as methyl sulfonate, trifluoromethane sulfonate, phenyl sulfonate, benzyl sulfonate, p-toluene sulfonate, trimethylbenzene sulfonate, triisobutyl benzene sulfonate, p-chlorobenzene sulfonate, and pentafluorobenzene sulfonate; sulfinate groups such as methyl sulfinate, phenyl sulfinate, benzyl sulfinate, p-toluene sulfinate, trimethylbenzene sulfinate, and pentafluorobenzene sulfinate; alkylthio groups; and arylthio groups. When the sulfur-containing group contains a carbon atom, the number of the carbon atom is 1 to 30, preferably 1 to 20.

The nitrogen-containing group is a group which has 1 to 5 nitrogen atoms in a group and which excludes a heterocyclic compound residue. Specific examples thereof include amino groups; alkyl amino groups such as methyl amino, dimethyl amino, diethyl amino, dipropyl amino, dibutyl amino, and dicyclohexyl amino; and aryl amino groups or alkyl aryl amino groups, such as phenyl amino, diphenyl amino, ditolyl amino, dinaphthyl amino, and methylphenyl amino.

The halogen-containing group is a group which has a halogen atom and which excludes a heterocyclic compound residue. Examples thereof include fluorine-containing groups such as $PF_6$ and $BF_4$, chlorine-containing groups such as $ClO_4$ and $SbCl_6$, and iodine-containing groups such as $IO_4$. The halogen-containing groups also include groups in which at least one hydrogen of the hydrocarbon groups having 1 to 20 carbon atoms is substituted with a halogen.

Examples of the heterocyclic compound residue include residues of nitrogen-containing compounds such as pyrrol, pyridine, pyrimidine, quinoline and triazine, oxygen-containing compounds such as furan and pyran, and sulfur-containing compounds such as thiophene; and groups in which these heterocyclic compound residues are further substituted with substituents such as alkyl groups and alkoxy groups having 1 to 30 carbon atoms, preferably 1 to 20 carbon atoms. The heterocyclic compound residues do not include the above nitrogen-containing groups, oxygen-containing group and sulfur-containing groups.

Y is a nitrogen atom, or a carbon atom having a substituent $R^{22}$, that is $—C(R^{22})=$.

G is an oxygen atom, a sulfur atom, a selenium atom, or a nitrogen atom having a substituent $R^{25}$, that is $—N(R^{25})—$.

$R^{21}$ to $R^{25}$ may be the same as or different from one another, and are an atom or a group selected from the group consisting of a hydrocarbon group, a halogen atom, a hydrogen atom, a hydrocarbon-substituted silyl group, an oxygen-containing group, a nitrogen-containing group, a sulfur-containing group, a boron-containing group, an aluminum-containing group, a phosphorus-containing group, a halogen-containing group, a heterocyclic compound residue, a silicon-containing group, a germanium-containing group, and a tin-containing group. Two or more of $R^{22}$ to $R^{25}$ may be united with one another to form a ring. When a is 2 or 3, $R^{21}$s, $R^{22}$s, $R^{23}$s, $R^{24}$s, and $R^{25}$s may be individually the same as or different from one another, and one group of $R^{22}$-$R^{25}$ contained in any one of the ligands and one group of $R^{22}$-$R^{25}$ contained in another ligand may be united.

Examples of the halogen atom, the oxygen-containing group, the nitrogen-containing group, the sulfur-containing group, the boron-containing group, the aluminum-containing group, the phosphorus-containing group, the heterocyclic compound residue, the silicon-containing group, the germanium-containing group, and the tin-containing group, represented by $R^{21}$ to $R^{25}$, can be those mentioned as the examples of X of the general formula (A). Examples of the halogen-containing group represented by $R^{21}$ to $R^{25}$ include those in which at least one hydrogen of a hydrocarbon group is substituted with a halogen, the hydrocarbon group having 1 to 30 carbon atoms, preferably 1 to 20 carbon atoms, e.g., alkyl groups such as methyl, ethyl, propyl, butyl, hexyl, octyl, nonyl, dodecyl, and eicosyl; cycloalkyl groups having 3 to 30 carbon atoms such as cyclopentyl, cyclohexyl, norbonyl, and adamantyl; alkenyl groups such as vinyl, propenyl, and cyclohexenyl; aryl alkyl groups such as benzyl, phenyl ethyl, and phenyl propyl; and aryl groups such as phenyl, tolyl, dimethyl phenyl, trimethyl phenyl, ethyl phenyl, propyl phenyl, biphenyl, naphthyl, methyl naphthyl, anthryl, and phenanthryl. Specific examples thereof include trifluoromethyl, perfluoromethyl, pentafluorophenyl, perfluorohexyl, trichloromethyl, perchloroethyl, pentachlorophenyl, and perchlorohexyl.

Example of the hydrocarbon group represented by $R^{21}$ to $R^{25}$ include those having 1 to 30 carbon atoms, and specific examples thereof include linear or branched alkyl groups having 1 to 30 carbon atoms, preferably 1 to 20 carbon atoms, such as methyl, ethyl, n-propyl, isopropyl, n-butyl, isobutyl, sec-butyl, tert-butyl, n-pentyl, neopentyl, and n-hexyl; linear or branched alkenyl groups having 2 to 30 carbon atoms, preferably 2 to 20 carbon atoms, such as vinyl, allyl, and isopropenyl; linear or branched alkynyl groups having 2 to 30 carbon atoms, preferably 2 to 20 carbon atoms, such as ethynyl, and propargyl; cyclic saturated hydrocarbon groups having 3 to 30 carbon atoms, preferably 3 to 20 carbon atoms, such as cyclopropyl, cyclobutyl, cyclopentyl, cyclohexyl, norbornyl, and adamantyl; cyclic unsaturated hydrocarbon groups having 5 to 30 carbon atoms, such as cyclopentadienyl, indenyl, and fluorenyl; aryl groups having 6 to 30 carbon atoms, preferably 6 to 20 carbon atoms, such as phenyl, benzyl, naphthyl, biphenyl, terphenyl, phenanthryl, and anthryl; and alkyl-substituted aryl groups, such as tolyl, isopropyl phenyl, tert-butyl phenyl, dimethyl phenyl, and di-tert-butyl phenyl. The above hydrocarbon groups may be substituted with other hydrocarbon groups, with examples thereof including aryl group-substituted alkyl groups such as benzyl and cumyl.

Examples of the hydrocarbon-substituted silyl group represented by $R^{21}$ to $R^{25}$ include groups with the total number of carbon atoms being 1 to 30. Specific examples thereof include methyl silyl, dimethyl silyl, trimethyl silyl, ethyl silyl, diethyl silyl, triethyl silyl, diphenylmethyl silyl, triphenyl silyl, dimethylphenylsilyl, dimethyl-t-butyl silyl, and dimethyl(pentafluorophenyl)silyl. Of these, preferable are methyl silyl, dimethyl silyl, trimethyl silyl, ethyl silyl, diethyl silyl, triethyl silyl, dimethylphenyl silyl, and triphenyl silyl. Particularly preferable are trimethyl silyl, triethyl silyl, triphenyl silyl, and dimethylphenyl silyl.

Of the transition metal compound (A), a transition metal compound (A1) represented by the following general formula is preferable.

[Chem. 29]

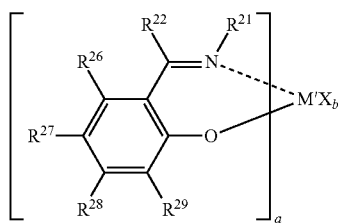

(A1)

In the general formula (A1), M', a, X, b, $R^{21}$, and $R^{22}$ are each defined in the same manner as in the general formula (A).

$R^{26}$ to $R^{29}$ may be the same as or different from one another, and are an atom or a group selected from the group consisting of a hydrogen atom, a hydrocarbon group, a halogen atom, a hydrocarbon-substituted silyl group, an oxygen-containing group, a nitrogen-containing group, a sulfur-containing group, a boron-containing group, an aluminum-containing group, phosphorus-containing group, a halogen-containing group, a heterocyclic compound residue, a silicon-containing group, a germanium-containing group, and a tin-containing group. Of these, two or more may be united with one another to form a ring. When a is 2 or 3, $R^{21}$s, $R^{22}$s, $R^{26}$s, $R^{27}$s, $R^{28}$s and $R^{29}$s may be individually the same as or different from one another, and one group of $R^{22}$ and $R^{26}$-$R^{29}$ contained in any one of the ligands and one group of $R^{22}$ and $R^{26}$-$R^{29}$ contained in another ligand may be united.

Examples of the hydrocarbon group, the halogen atom, the hydrocarbon-substituted silyl group, the oxygen-containing group, the nitrogen-containing group, the sulfur-containing group, the boron-containing group, the aluminum-containing group, the phosphorus-containing group, the halogen-containing group, the heterocyclic compound residue, the silicon-containing group, the germanium-containing group, and the tin-containing group, represented by $R^{26}$ to $R^{29}$, can be those mentioned as the examples of those represented by $R^{22}$ to $R^{25}$.

As the transition metal compounds (A) and (A1), those described in JP-A-2000-191713, JP-A-2000-239312, WO01/055231 pamphlet, JP-A-2003-40953, or the like can be employed as needed.

In the method of the present invention, as the transition metal compound (A), a single kind of compound can be employed solely, but as needed, two or more kinds of the transition metal compound (A) different in structure can be combined and employed.

Diene Compound (B)

The diene compound (B) employed in the method for producing the organometallic compound (1) of the present invention is a compound represented by the following general formula.

[Chem. 30]

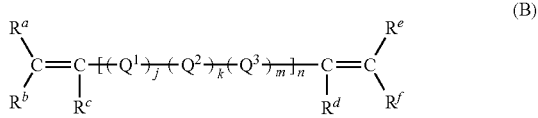

(B)

In the general formula (B), $Q^1$, $Q^2$, $Q^3$, j, k, m, and n are each defined in the same manner as in the general formula (1).

$R^a$ to $R^f$ are each independently a hydrogen atom, or a hydrocarbon group having 1 to 20 carbon atoms, and may be a group formed by substituting a part of the hydrogen atoms of the hydrocarbon group with a substituent containing a heteroatom excluding carbon and hydrogen. Examples of the hydrocarbon group include alkyl groups, aryl groups, and aryl alkyl groups having 1 to 20 carbon atoms. Specific examples thereof include methyl group, ethyl group, propyl group, isopropyl group, n-butyl group, sec-butyl group, tert-butyl group, isobutyl group, pentyl group, hexyl group, octyl group, decyl group, cyclohexyl group, phenyl group, tolyl group, naphthyl group, benzyl group, and 2-phenylethyl group. As $R^a$ to $R^f$, of the above atom and groups, preferable are a hydrogen atom, methyl group, ethyl group, propyl group, phenyl group, benzyl group, 2-phenylethyl group, and more preferable are a hydrogen atom, methyl group, ethyl group, and phenyl group, and still more preferable are a hydrogen atom, and methyl group.

Specific examples of the diene compound include
conjugated diene compounds such as 1,3-butadiene, 1,3-pentadiene, 1,3-hexadiene, 1,3-heptadiene, 1,3-octadiene, 1-phenyl-1,3-butadiene, 1-phenyl-2,4-pentadiene, isoprene, 2-ethyl-1,3-butadiene, 2-propyl-1,3-butadiene, 2-butyl-1,3-butadiene, 2-pentyl-1,3-butadiene, 2-hexyl-1,3-butadiene, 2-heptyl-1,3-butadiene, 2-octyl-1,3-butadiene, and 2-phenyl-1,3-butadiene;

chain non-conjugated diene compounds such as 1,4-pentadiene, 3-methyl-1,4-pentadiene, 1,4-hexadiene, 3-methyl-1,4-hexadiene, 4-methyl-1,4-hexadiene, 5-methyl-1,4-hexadiene, 4,5-dimethyl-1,4-hexadiene, 1,5-hexadiene, 3-methyl-1,5-hexadiene, 1,5-heptadiene, 3-methyl-1,5-heptadiene, 1,6-heptadiene, 4-methyl-1,6-heptadiene, 1,6-octadiene, 4-methyl-1,6-octadiene, 7-methyl-1,6-octadiene, 1,7-octadiene, 4-methyl-1,7-octadiene, 1,7-nonadiene, 4-methyl-1,7-nonadiene, 1,8-nonadiene, 4-methyl-1,8-nonadiene, 1,8-decadiene, 5-methyl-1,8-decadiene, 1,9-decadiene, 5-methyl-1,9-decadiene, 1,10-undecadiene, and 1,11-dodecadiene;

triene compounds such as 1,4,7-octatriene, 3-methyl-1,4,7-octatriene, 1,5,9-decatriene, and 4-methyl-1,5,9-decatriene;

cyclic olefin compounds such as 5-methylene-2-norbornene, 5-vinyl-2-norbornene, 5-(2-propenyl)-2-norbornene, 5-(3-butenyl)-2-norbornene, 5-(1-methyl-2-propenyl)-2-norbornene, 5-(4-pentenyl)-2-norbornene, 5-(1-methyl-3-butenyl)-2-norbornene, 5-(5-hexenyl)-2-norbornene, 5-(1-methyl-4-pentenyl)-2-norbornene, 5-(2,3-dimethyl-3-butenyl)-2-norbornene, 5-(2-ethyl-3-butenyl)-2-norbornene, 5-(6-heptenyl)-2-norbornene, 5-(3-methyl-5-hexenyl)-2-norbornene, 5-(3,4-dimethyl-4-pentenyl)-2-norbornene, 5-(3-ethyl-4-pentenyl)-2-norbornene, 5-(7-octenyl)-2-norbornene, 5-(2-methyl-6-heptenyl)-2-norbornene, 5-(1,2-dimethyl-5-hexenyl)-2-norbornene, 5-(5-ethyl-5-hexenyl)-2-norbornene, 5-(1,2,3-trimethyl-4-pentenyl)-2-norbornene, dicyclopentadiene, 5-ethylidene-2-norbornene, 5-isopropylidene-2-norbornene, 1,1'-bi(3-cyclopentene), di(3-cyclopentenyl)methane, 1,3-di(3-cyclopentenyl)propane, 1,4-di(3-cyclopentenyl)butane, 1,5-di(3-cyclopentenyl)pentane, 3-methyl-1,1'-bi(3-cyclopentene), 4-(3-cyclopentenylmethyl)-1 ethyl-1-cyclopentene, 4-(3-(3-cyclopentenyl)propyl)-1-methyl-1-cyclopentene, 4-(4-(3-cyclopentenyl)butyl)-1-methyl-1-cyclopentene, 1,1'-bi(3-cyclohexene), di(3-cyclohexenyl)methane, 1,3-di(3-cyclohexenyl)propane, 1,4-di(3-cyclohexenyl)butane, and 1,5-di(3-cyclohexenyl)pentane;

cyclic diene compounds such as 6-chloromethyl-5-isopropenyl-2-norbornene;

halogen-containing diene compounds such as 3-chloro-1,4-pentadiene, 3-bromo-3-methyl-1,4-pentadiene, 3-chloro-1,4-hexadiene, 3-chloro-3-methyl-1,4-hexadiene, 3-bromo-4-methyl-1,4-hexadiene, 3-chloro-5-methyl-1,4-hexadiene, 3-bromo-4,5-dimethyl-1,4-hexadiene, 3-bromo-1,5-hexadiene, 3-chloro-3-methyl-1,5-hexadiene, 3-bromo-1,5-heptadiene, 3-chloro-3-methyl-1,5-heptadiene, 4-bromo-1,6-heptadiene, 3-chloro-4-methyl-1,6-heptadiene, 4-bromo-1,6-octadiene, 3-chloro-4-methyl-1,6-octadiene, 4-bromo-7-methyl-1,6-octadiene, 4-chloro-1,7-octadiene, 3-chloro-4-methyl-1,7-octadiene, 4-bromo-1,7-nonadiene, 4-bromo-4-methyl-1,7-nonadiene, 4-bromo-1,8-nonadiene, 3-chloro-4-methyl 1,8-nonadiene, 5-bromo-1,8-decadiene, 3-chloro-5-methyl-1,8-decadiene, 5-bromo-1,9-decadiene, 3-chloro-5-methyl-1,9-decadiene, 5-bromo-1,10-undecadiene, and 5-bromo-1,1'-dodecadiene;

silane-containing dienes such as bisvinyloxy silane, dimethyl bisvinyloxy silane, bisallyloxy silane, dimethylbis allyloxy silane, di(3-butenyl)dimethyl silane, bis(3-butenyloxy) silane, dimethylbis(3-butenyloxy)silane, di(4-pentenyl) dimethyl silane, bis(4-pentenyloxy)silane, bis(4-pentenyloxy)dimethylsilane, di(5-hexenyl)dimethylsilane, bis(5-hexenyloxy)silane, and bis(5-hexenyloxy)dimethylsilane;

ester-containing diene compounds such as 3-butenyl-4-pentenoate, 4-pentenyl-4-pentenoate, 4-methoxycarbonyl-1,7-octadiene, and 4-methoxycarbonyl-1,9-decadiene;

ether-containing diene compounds such as divinyl ether, diallyl ether, di(4-butenyloxy)ether, and di(5-hexenyloxy) ether;

siloxy-containing diene compounds such as 4-trimethyl siloxymethyl-1,7-octadiene, and 4-trimethyl siloxymethyl-1,9-decadiene.

These diene compounds are generally available or can be produced by known methods.

In the method of the present invention, as the diene compound (B), a single kind of compound can be employed solely, but as needed, two or more kinds of the diene compound (B) different in structure can be combined and employed.

Organometallic Compound (C)

An organometallic compound (C) employed to produce the organometallic compound (1) of the present invention is a compound represented by the following general formula.

[Chem. 31]

R-M-R (C)

In the general formula (C), M is a magnesium atom, a zinc atom, an Al—$R^{11}$ group, or a Ga—$R^{11}$ group, and $R^{11}$ is a hydrogen atom, a hydrocarbon group, a halogen atom, a silicon-containing group, or an oxygen-containing group. Examples of the hydrocarbon group, the halogen atom, the silicon-containing group, the oxygen-containing group, represented by $R^{11}$, can be mentioned as the examples defined for the general formula (1). M is preferably a zinc atom or an Al—$R^{11}$ group, more preferably a zinc atom.

Two Rs are each independently a hydrocarbon group having 1 to 20 carbon atoms, and may be a group formed by substituting a part of the hydrogen atoms of the hydrocarbon group with a substituent containing a heteroatom excluding carbon and hydrogen.

Examples of the hydrocarbon group, represented by R, include alkyl groups, aryl groups, and aryl alkyl groups, having 1 to 20 carbon atoms. Specific examples thereof include methyl group, ethyl group, propyl group, isopropyl group, n-butyl group, isobutyl group, sec-butyl group, tert-butyl group, pentyl group, neopentyl group, hexyl group, octyl group, decyl group, cyclohexyl group, phenyl group, tolyl group, naphthyl group, benzyl group, 2-phenylethyl group, trimethyl silyl methyl group, triethyl silyl methyl group, trimethoxy silyl methyl group, triisopropyl silyl methyl group, triphenyl silyl methyl group, tert-butyl dimethyl silyl methyl group, trimethyl silyl ethyl group, triethyl silyl ethyl group, trimethoxy silyl ethyl group, triisopropyl silyl ethyl group, triphenyl silyl ethyl group, and tert-butyl dimethyl silyl ethyl group. Of these hydrocarbon groups, preferable are methyl group, ethyl group, propyl group, isopropyl group, n-butyl group, isobutyl group, sec-butyl group, tert-butyl group, neopentyl group, octyl group, phenyl group, benzyl group, trimethyl silyl methyl group, and triethyl silyl methyl group; and more preferable are methyl group, ethyl group, isopropyl group, isobutyl group, tort-butyl group, phenyl group, benzyl group, and trimethyl silyl methyl group; and still more preferable are methyl group, ethyl group, isopropyl group, phenyl group, and trimethyl silyl methyl group. These are employed singly or in combination of two or more kinds.

Specific examples of the organometallic compound (C) include:

organomagnesium compounds such as dibutyl magnesium, and dihexyl magnesium, organozinc compounds such as dimethyl zinc, diethylzinc, dipropyl zinc, diisopropyl zinc, dibutyl zinc, diphenyl zinc, dibenzyl zinc, and bis(trimethylsilylmethyl)zinc;

organoaluminum compounds such as tri-n-alkyl aluminums e.g., trimethyl aluminum, triethyl aluminum, tri-n-butyl aluminum, tripropyl aluminum, tripentyl aluminum, trihexyl aluminum, trioctyl aluminum, and tridecyl aluminum; tribranched alkyl aluminums, e.g., triisopropyl aluminum, triisobutyl aluminum, tri-sec-butyl aluminum, tri-tert-butyl aluminum, tri-2-methyl butyl aluminum, tri-3-methyl butyl aluminum, tri-2-methyl pentyl aluminum, tri-3-methyl pentyl aluminum, tri-4-ethyl pentyl aluminum, tri-2-methyl hexyl aluminum, tri-3-methyl hexyl aluminum, and tri-2-ethyl hexyl aluminum; tricycloalkyl aluminums, e.g., tricyclohexyl aluminum, and tricyclooctyl aluminum; triaryl aluminums, e.g., triphenyl aluminum, and tritolyl aluminum; dialkyl aluminum hydrides, e.g., diisobutyl aluminum hydride; and organogallium compounds such as trimethyl gallium, triethyl gallium, tripropyl gallium, and tributyl gallium.

In the present invention, as the organometallic compound (C), a single kind of compound can be employed solely, but as needed, two or more kinds of the organometallic compound (C) different in structure can be combined and employed.

Regarding these organometallic compounds, it has been known that mixing organometallic compounds having the same metal allows substituent exchange to proceed. In other words, employing two or more kinds of organometallic compounds having the same metal in an arbitral ratio can result in the effect of providing an organometallic compound having an arbitral substituent in an arbitral ratio.

Furthermore, by sequentially adding two or more organometallic compounds different in reactivity, or by previously mixing such compounds and adding the mixture, it is possible to preferentially introduce arbitral substituents into terminals represented by $R^1$ and $R^{10}$ in the general formula (1), utilizing the two different kinds of reactivities. Thereby, the reactivity at the terminals can be controlled.

These organometallic compounds (C) are easily available on an industrial basis, or can be synthesized by known methods such as halogen metal exchange and metal exchange.

Co-Catalyst Component (D)

In the method for producing the organometallic compound (1) of the present invention, in the presence of the transition metal compound (A) as a catalyst, the diene compound (B) is reacted with the organometallic compound (C). In a preferable embodiment of the production, together with the transition metal compound (A) as a catalyst, a co-catalyst component (D) is used. Examples of the co-catalyst component (D) include at least one compound selected from:

(D-1) an organometallic compound,
(D-2) an organoaluminum oxy-compound, and
(D-3) a compound that reacts with the transition metal compound to form an ion pair.

(D-1) Specific examples of the organometallic compound include organometallic compounds of Groups 1, 2, 12, and 13 of the periodic table, as described below.

(D-1a) Organoaluminum compounds represented by the general formula: $R^a{}_m Al(OR^b)_n H_p X_q$ In the formula, $R^a$ and $R^b$ may be the same as or different from one another, and are hydrocarbon groups having 1 to 15 carbon atoms, preferably 1 to 4 carbon atoms; X is a halogen atom; and m satisfies $0<m\leq3$, n satisfies $0\leq n<3$, p satisfies $0\leq p<3$, and q satisfies $0\leq q<3$, and $m+n+p+q=3$.

(D-1b) Alkyl complex compounds containing a Group 1 metal of the periodic table and aluminum and represented by the following formula: $M^2 AlR^a{}_4$ In the formula, $M^2$ is Li, Na or K; and $R^a$ is a hydrocarbon group having 1 to 15 carbon atoms, and preferably 1 to 4 carbon atoms.

(D-1c) Dialkyl compounds containing a Group 2 or Group 12 metal of the periodic table and represented by the following formula: $R^a R^b M^3$ In the formula, $R^a$ and $R^b$ may be the same as or different from one another, and are each a hydrocarbon group having 1 to 15 carbon atoms, and preferably 1 to 4 carbon atoms; and $M^3$ is Mg, Zn or Cd.

Examples of the organoaluminum compounds (D-1a) include:

organoaluminum compounds represented by the following formula: $R^a{}_m Al(OR^b)_{3-m}$ In the formula, $R^a$ and $R^b$ may be the same as or different from each other, and are each a hydrocarbon group having 1 to 15, and preferably 1 to 4 carbon atoms; and m preferably satisfies $1.5\leq m\leq3$;

organoaluminum compounds represented by the following formula: $R^a{}_m AlX_{3-m}$ In the formula, $R^a$ is a hydrocarbon group having 1 to 15 carbon atoms, and preferably 1 to 4 carbon atoms; X is a halogen atom; and m preferably satisfies $0<m<3$;

organoaluminum compounds represented by the following formula: $R^a{}_m AlH_{3-m}$ In the formula, $R^a$ is a hydrocarbon group having 1 to 15 carbon atoms, and preferably 1 to 4 carbon atoms; and m preferably satisfies $2\leq m<3$; and organoaluminum compounds represented by the following formula: $R^a{}_m Al(OR^b)_n X_q$ In the formula, $R^a$ and $R^b$ may be the same as or different from each other, and are each a hydrocarbon group having 1 to 15 carbon atoms, and preferably 1 to 4 carbon atoms; X is a halogen atom; m satisfies $0<m\leq3$, n satisfies $0\leq n<3$, q satisfies $0\leq q<3$ and $m+n+q=3$.

Specific examples of the organoaluminum compound belonging to (D-1a) include tri(n-alkyl)aluminums such as trimethylaluminum, triethylaluminum, tri(n-butyl)aluminum, tripropylaluminum, tripentylaluminum, trihexylaluminum, trioctylaluminum and tridecylaluminum;

branched-chain trialkylaluminums such as triisopropylaluminum, triisobutylaluminum, tri(sec-butyl)aluminum, tri(tert-butyl)aluminum, tri(2-methylbutyl)aluminum, tri(3-methylbutyl)aluminum, tri(2-methylpentyl)aluminum, tri(3-methylpentyl)aluminum, tri(4-methylpentyl)aluminum, tri(2-methylhexyl)aluminum, tri(3-methylhexyl)aluminum and tri(2-ethylhexyl)aluminum;

tricycloalkylaluminums such as tricyclohexylaluminum and tricyclooctylaluminum;

triarylaluminums such as triphenylaluminum and tritolylaluminum;

dialkylaluminum hydrides such as diisobutylaluminum hydride;

trialkenylaluminums such as those represented by the formula $(i\text{-}C_4H_9)_x Al_y (C_5H_{10})_z$ (wherein x, y and z are each a positive number, and $z\geq -2x$) with examples including triisoprenylaluminum;

alkylaluminum alkoxides such as isobutylaluminum methoxide, isobutylaluminum ethoxide and isobutylaluminum isopropoxide;

dialkylaluminum alkoxides such as dimethylaluminum methoxide, diethylaluminum ethoxide and dibutylaluminum butoxide;

alkylaluminum sesquialkoxides such as ethylaluminum sesquiethoxide and butylaluminum sesquibutoxide;

partially alkoxylated alkylaluminums such as those having an average composition represented by $R^a{}_{2.5}Al(OR^b)_{0.5}$;

dialkylaluminum aryloxides such as diethylaluminum phenoxide, diethylaluminum(2,6-di-t-butyl-4-methylphenoxide), ethylaluminumbis(2,6-di-t-butyl-4-methylphenoxide), diisobutylaluminum(2,6-di-t-butyl-4-methylphenoxide) and isobutylaluminumbis(2,6-di-t-butyl-4-methylphenoxide);

dialkylaluminum halides such as dimethylaluminum chloride, diethylaluminum chloride, dibutylaluminum chloride, diethylaluminum bromide and diisobutylaluminum chloride;

alkylaluminum sesquihalides such as ethylaluminum sesquichloride, butylaluminum sesquichloride and ethylaluminum sesquibromide;

partially halogenated alkylaluminums such as alkylaluminum dihalides including ethylaluminum dichloride, propylaluminum dichloride and butylaluminum dibromide;

dialkylaluminum hydrides such as diethylaluminum hydride and dibutylaluminum hydride;

partially hydrogenated alkylaluminums such as alkylaluminum dihydrides including ethylaluminum dihydride and propylaluminum dihydride; and partially alkoxylated and halogenated alkylaluminums such as ethylaluminum ethoxychloride, butylaluminum butoxychloride and ethylaluminum ethoxybromide.

Compounds analogous to (D-1a) are also employable. Examples of such compounds include organoaluminum compounds wherein two or more aluminum compounds are bonded via a nitrogen atom, such as $(C_2H_5)_2AlN(C_2H_5)Al(C_2H_5)_2$.

Examples of the compounds belonging to (D-1b) include $LiAl(C_2H_5)_4$ and $LiAl(C_7H_{15})_4$.

Examples of other compounds as the organometallic compounds (D-1) include methyllithium, ethyllithium, propyllithium, butyllithium, methylmagnesium bromide, methylmagnesium chloride, ethylmagnesium bromide, ethylmagnesium chloride, propylmagnesium bromide, propylmagnesium chloride, butylmagnesium bromide, butylmagnesium chloride, dimethyl magnesium, diethyl magnesium, dibutyl magnesium, and butylethyl magnesium.

Combinations of compounds capable of forming the above organoaluminum compounds in the system are also employable, with examples including a combination of aluminum halide and alkyllithium and a combination of aluminum halide and alkylmagnesium.

Of the organometallic compounds (D-1), the organoaluminum compounds are preferable. The organometallic compounds (D-1) are used singly, or two or more kinds are used in combination.

The organoaluminum oxy-compounds (D-2) may be conventional aluminoxanes or benzene-insoluble organoaluminum oxy-compounds as described in JP-A-H02-78687.

For example, conventional aluminoxane can be prepared by the following processes, and is generally obtained as a solution in a hydrocarbon solvent.

(1) An organoaluminum compound such as trialkylaluminum is added to a hydrocarbon medium suspension of a compound containing water of adsorption or a salt containing water of crystallization, e.g., magnesium chloride hydrate, copper sulfate hydrate, aluminum sulfate hydrate, nickel sulfate hydrate or cerous chloride hydrate, to allow the organoaluminum compound to react with the water of adsorption or the water of crystallization.

(2) Water, ice or water vapor is allowed to directly act on an organoaluminum compound such as trialkylaluminum in a medium such as benzene, toluene, ethyl ether or tetrahydrofuran.

(3) An organotin oxide such as dimethyltin oxide or dibutyltin oxide is allowed to react with an organoaluminum compound such as trialkylaluminum in a medium such as decane, benzene or toluene.

The aluminoxane may contain a small amount of an organometallic component. Further, the solvent or the unreacted organoaluminum compound may be distilled off from the solution of aluminoxane collected, and the distillate may be redissolved in a solvent or suspended in a poor solvent for the aluminoxane.

Examples of the organoaluminum compounds used in the preparation of aluminoxanes include the organoaluminum compounds described above for the organoaluminum compounds belonging to (D-1a).

Of these, the trialkylaluminums and tricycloalkylaluminums are preferable, and trimethylaluminum is particularly preferable. The organoaluminum compounds are used singly, or two or more kinds are used in combination.

Examples of the solvents used in the preparation of aluminoxanes include aromatic hydrocarbons such as benzene, toluene, xylene, cumene and cymene; aliphatic hydrocarbons such as pentane, hexane, heptane, octane, decane, dodecane, hexadecane and octadecane; alicyclic hydrocarbons such as cyclopentane, cyclohexane, cyclooctane and methylcyclopentane; petroleum fractions such as gasoline, kerosine and light oil; and halides such as chlorides and bromides of these aromatic, aliphatic and alicyclic hydrocarbons. Ethers such as ethyl ether and tetrahydrofuran are also employable. Of the solvents, the aromatic hydrocarbons or the aliphatic hydrocarbons are particularly preferable.

The benzene-insoluble organoaluminum oxy-compound contains an Al component which is soluble in benzene at 60° C., usually in an amount of not more than 10%, preferably not more than 5%, and particularly preferably not more than 2% in terms of Al atom. That is, the benzene-insoluble organoaluminum oxy-compound is preferably insoluble or hardly soluble in benzene.

Examples of the organoaluminum oxy-compounds further include boron-containing organoaluminum oxy-compounds represented by the following formula (III):

[Chem. 32]

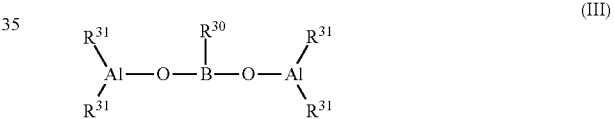

(III)

In the formula, $R^{30}$ is a hydrocarbon group having 1 to 10 carbon atoms; and $R^{31}$ may be the same as or different from one another, and are each a hydrogen atom, a halogen atom, or a hydrocarbon group having 1 to 10 carbon atoms.

The boron-containing organoaluminum oxy-compounds represented by the general formula (III) can be prepared by allowing an alkylboronic acid represented by the general formula (IV):

[Chem. 33]

$R^{30}$—$B(OH)_2$ (IV)

(in the formula, $R^{30}$ is the same group as described above), to react with an organoaluminum compound in an inert solvent at a temperature of −80° C. to room temperature for 1 minute to 24 hours under an inert gas atmosphere.

Examples of the alkylboronic acids represented by the general formula (IV) include methylboronic acid, ethylboronic acid, isopropylboronic acid, n-propylboronic acid, n-butylboronic acid, isobutylboronic acid, n-hexylboronic acid, cyclohexylboronic acid, phenylboronic acid, 3,5-difluoroboronic acid, pentafluorophenylboronic acid and 3,5-bis(trifluoromethyl)phenylboronic acid. Of these, methylboronic acid, n-butylboronic acid, isobutylboronic acid, 3,5-difluorophenylboronic acid and pentafluorophenylboronic acid are preferable. These are used singly, or two or more kinds are used in combination.

Examples of the organoaluminum compounds to be reacted with the alkylboronic acids include the organoaluminum compounds described above for the organoaluminum compounds belonging to (D-1a).

Of these, the trialkylaluminums and tricycloalkylaluminums are preferable, and trimethylaluminum, triethylaluminum and triisobutylaluminum are particularly preferable. These are used singly, or two or more kinds are used in combination.

The organoaluminum oxy-compounds (D-2) mentioned above are used singly, or two or more kinds are used in combination.

The compounds (D-3) that react with the transition metal compound to form an ion pair (hereinafter, called "ionized ionic compounds") are compounds that react with the transition metal compound represented by the general formula (A) to form an ion pair. Examples of such compounds include Lewis acids, ionic compounds, borane compounds and carborane compounds as described in JP-A-H01-501950, JP-A-H01-502036, JP-A-H03-179005, JP-A-H03-179006, JP-A-H03-207703, JP-A-H03-207704, and U.S. Pat. No. 5,321,106. Heteropoly compounds and isopoly compounds may also be employed.

The Lewis acids include compounds represented by $BR_3$ (R is fluorine, or a phenyl group which may have a substituent such as fluorine, methyl group or trifluoromethyl group). Specific examples include trifluoroboron, triphenylboron, tris(4-fluorophenyl)boron, tris(3,5-difluorophenyl)boron, tris(4-fluoromethylphenyl)boron, tris(pentafluorophenyl)boron, tris(p-tolyl)boron, tris(o-tolyl)boron and tris(3,5-dimethylphenyl)boron.

The ionic compounds include compounds represented by the following general formula (V):

[Chem. 34]

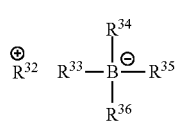

(V)

In the above formula, $R^{32}$ is, for example, $H^+$ carbonium cation, oxonium cation, ammonium cation, phosphonium cation, cycloheptyltrienyl cation, or ferrocenium cation having a transition metal.

$R^{33}$ to $R^{36}$ may be the same as or different from one another, and are each an organic group, and preferably an aryl group or a substituted aryl group. Examples of the carbonium cations include tri-substituted carbonium cations such as triphenylcarbonium cation, tri(methylphenyl)carbonium cation and tri(dimethylphenyl)carbonium cation.

Examples of the ammonium cations include trialkylammonium cations such as tri ethylammonium cation, triethylammonium cation, tripropylammonium cation, tributylammonium cation and tri(n-butyl)ammonium cation; N,N-dialkylanilinium cations such as N,N-dimethylanilinium cation, N,N-diethylanilinium cation and N,N,2,4,6-pentamethylanilinium cation; and dialkylammonium cations such as di(isopropyl)ammonium cation and dicyclohexylammonium cation.

Examples of the phosphonium cations include triarylphosphonium cations such as triphenylphosphonium cation, tri(methylphenyl)phosphonium cation and tri(dimethylphenyl)phosphonium cation.

$R^{32}$ is preferably carbonium cation or ammonium cation, and particularly preferably triphenylcarbonium cation, N,N-dimethylanilinium cation, or N,N-diethylanilinium cation.

Examples of the ionic compounds further include trialkyl-substituted ammonium salts, N,N-dialkylanilinium salts, dialkylammonium salts and triarylphosphonium salts.

Specific examples of the trialkyl-substituted ammonium salts include triethylammonium tetraphenylborate, tripropylammonium tetraphenylborate, tri(n-butyl)ammonium tetraphenylborate, trimethylammonium tetra(p-tolyl)borate, trimethylammonium tetra(o-tolyl)borate, tri(n-butyl)ammonium tetra(pentafluorophenyl)borate, tripropylammonium tetra(o,p-dimethylphenyl)borate, tri(n-butyl)ammonium tetra(m,m-dimethylphenyl)borate, tri(n-butyl)ammonium tetra(p-trifluoromethylphenyl)borate, tri(n-butyl)ammonium tetra(3,5-ditrifluoromethylphenyl)borate and tri(n-butyl)ammonium tetra(o-tolyl)borate.

Examples of the N,N-dialkylanilinium salts include N,N-dimethylanilinium tetraphenylborate, N,N-diethylanilinium tetraphenylborate and N,N,2,4,6-pentamethylanilinium tetraphenylborate.

Examples of the dialkylammonium salts include di(1-propyl)ammonium tetra(pentafluorophenyl)borate and dicyclohexylammonium tetraphenylborate.

Examples of the ionic compounds further include triphenylcarbenium tetrakis(pentafluorophenyl)borate, N,N-dimethylanilinium tetrakis(pentafluorophenyl)borate, ferrocenium tetra(pentafluorophenyl)borate, triphenylcarbenium pentaphenylcyclopentadienyl complex, N,N-diethylanilinium pentaphenylcyclopentadienyl complex, and boron compounds represented by the following general formula (VI) or (VII).

[Chem. 35]

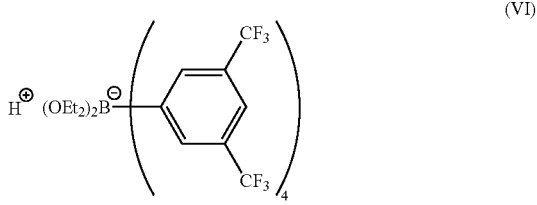

(VI)

(in the formula, Et denotes ethyl group.)

[Chem. 36]

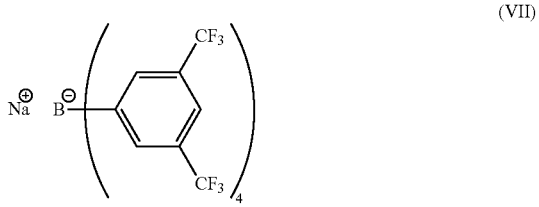

(VII)

Examples of the borane compounds include:
decaborane (14);
salts of anions such as bis[tri(n-butyl)ammonium]nonaborate, his[tri(n-butyl)ammonium]decaborate, bis[tri(n-butyl)ammonium]undecaborate, bis[tri(n-butyl)ammonium]dodecaborate, bis[tri(n-butyl)ammonium]decachlorodecaborate and bis[tri(n-butyl)ammonium]dodecachlorododecaborate; and salts of metal borane anions such as tri(n-butyl)ammonium bis(dodecahydridododecaborate) cobaltate (III) and bis[tri(n-butyl)ammonium]bis(dodecahydridododecaborate) nickelate (III).

Examples of the carborane compounds include:

salts of anions such as 4-carbanonaborane (14), 1,3-dicarbanonaborane (13), 6,9-dicarbadecaborane (14), dodecahydrido-1-phenyl-1,3-dicarbanonaborane, dodecahydrldo-1-methyl-1,3-dicarbanonaborane, undecahydrido-1,3-dimethyl-1,3-dicarbanonaborane, 7,8-dicarbaundecaborane (13), 2,7-dicarbaundecaborane (13), undecahydrido-7,8-dimethyl-7,8-dicarbaundecaborane, dodecahydrido-11-methyl-2,7-dicarbaundecaborane, tri(n-butyl)ammonium-1-carbadecaborate, tri(n-butyl)ammonium-1-carbaundecaborate, tri(n-butyl)ammonium-1-carbadodecaborate, tri(n-butyl)ammonium-1-trimethylsilyl-1-carbadecaborate, tri(n-butyl)ammoniumbromo-1-carbadodecaborate, tri(n-butyl)ammonium-6-carbadecaborate (14), tri(n-butyl)ammonium-6-carbadecaborate (12), tri(n-butyl)ammonium-7-carbaundecaborate (13), tri(n-butyl)ammonium-7,8-dicarbaundecaborate (12), tri(n-butyl)ammonium-2,9-dicarbaundecaborate (12), tri(n-butyl)ammonium dodecahydrido-8-methyl-7,9-dicarbaundecaborate, tri(n-butyl)ammonium undecahydrido-8-ethyl-7,9-dicarbaundecaborate, tri(n-butyl)ammonium undecahydrido-8-butyl-7,9-dicarbaundecaborate, tri(n-butyl)ammonium undecahydrido-8-allyl-7,9-dicarbaundecaborate, tri(n-butyl)ammonium undecahydrido-9-trimethylsilyl-7,8-dicarbaundecaborate and tri(n-butyl)ammonium undecahydrido-4,6-dibromo-7-carbaundecaborate; and salts of metal carborane anions such as tri(n-butyl)ammonium bis(nonahydrido-1,3-dicarbanonaborate) cobaltate (III), tri(n-butyl)ammonium bis(undecahydrido-7,8-dicarbaundecaborate) ferrate (III), tri(n-butyl)ammonium bis(undecahydrido-7,8-dicarbaundecaborate) cobaltate (III), tri(n-butyl)ammonium bis(undecahydrido-7,8-dicarbaundecaborate) nickelate (III), tri(n-butyl)ammonium bis(undecahydrido-7,8-dicarbaundecaborate) cuprate (III), tri(n-butyl)ammonium bis(undecahydriclo-7,8-dicarbaundecaborate) aurate (III), tri(n-butyl)ammonium bis(nonahydrido-7,8-dimethyl-7,8-dicarbaundecaborate) ferrate (III), tri(n-butyl)ammonium bis(nonahydrido-7,8-dimethyl-7,8-dicarbaunclecaborate) chromate (III), tri(n-butyl)ammonium bis(tribromooctahydrido-7,8-dicarbaundecaborate) cobaltate (III), tris[tri(n-butyl)ammonium]bis(undecahydrido-7-carbaundecaborate) chromate (III), bis[tri(n-butyl)ammonium]bis(undecahydrido-7-carbaundecaborate) manganate (IV), bis[tri(n-butyl)ammonium]bis(undecahydrido-7-carbaundecaborate) cobaltate (III) and bis[tri(n-butyl)ammonium]bis(undecahydrido-7-carbaundecaborate) nickelate (IV).

The heteropoly compounds contain an atom selected from silicon, phosphorus, titanium, germanium, arsenic and tin, and one or more atoms selected from vanadium, niobium, molybdenum and tungsten. Examples of such compounds include, although not limited thereto, phosphovanadic acid, germanovanadic acid, arsenovanadic acid, phosphoniobic acid, germanoniobic acid, siliconomolybdic acid, phosphomolybdic acid, titanomolybdic acid, germanomolybdic acid, arsenomolybdic acid, stannomolybdic acid, phosphotungstic acid, germanotungstic acid, stannotungstic acid, phosphomolybdovanadic acid, phosphotungstovanadic acid, germanotungstovanadic acid, phosphomolybdotungstovanadic acid, germanomolybdotungstovanadic acid, phosphomolybdotungstic acid, phosphomolybdoniobic acid; salts of these acids such as salts of these acids with metals of Group 1 or Group 2 of the periodic table such as lithium, sodium, potassium, rubidium, cesium, beryllium, magnesium, calcium, strontium and barium; and organic salts of the above acids such as triphenylethyl salts.

The above (D-3) ionized ionic compounds are used singly, or two or more kinds are used in combination.

In the production of the organometallic compound (1) of the present invention, the transition metal compound (A) may be used singly. Alternatively, with the transition metal compound (A), at least one co-catalyst component (D) selected from the organometallic compound (D-1), the organoaluminum oxy-compound (D-2), and the compound (D-3) that reacts with the transition metal compound to form an ion pair may be used.

In the present invention, the organometallic compound (C) and the co-catalyst component (5) may be the same compound.

Carrier (E)

In the production of the organometallic compound (1) of the present invention, with the transition metal compound (A), and optionally with at least one co-catalyst component (D) selected from the organometallic compound (D-1), the organoaluminum oxy-compound (D-2), and the ionized ionic compound (D-3), a carrier (E), described below, and/or an organic compound component (F), described later, can be further used as needed.

The carrier (E) is an inorganic or an organic compound in the form of granular or fine particulate solid.

Preferred inorganic compounds include porous oxides, inorganic halides, clay minerals and ion-exchange layered compounds excluding the clay minerals. Examples of the porous oxides include $SiO_2$, $Al_2O_3$, $MgO$, $ZrO$, $TiO_2$, $B_2O_3$, $CaO$, $ZnO$, $BaO$, $ThO_2$, and complex compounds or mixtures containing these oxides, such as natural or synthetic zeolite, $SiO_2$—$MgO$, $SiO_2$—$Al_2O_3$, $SiO_2$—$TiO2$, $SiO$—$V_2O_5$, $SiO_2$—$Cr_2O_3$ and $SiO_2$—$TiO_2$—$MgO$. Of these, compounds containing $SiO_2$ and/or $Al_2O_3$ as a main component are preferable.

The inorganic oxides may contain small amounts of carbonate, sulfate, nitrate and oxide components such as $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2O$.

The porous oxides have different properties depending on type and preparation process. The carrier used in the present invention preferably has a particle diameter of 10 to 300 μm, preferably 20 to 200 μm, a specific surface area of 50 to 1,000 $m^2/g$, preferably 100 to 700 $m^2/g$, and a pore volume of 0.3 to 3.0 $cm^3/g$. If necessary, the carrier may be calcined at 100 to 1000° C., and preferably 150 to 700° C. prior to use.

Examples of the inorganic halides include $MgCl_2$, $MgBr_2$, $MnCl_2$ and $MnBr_2$. The inorganic halides may be used as they are, or may be used after pulverized with a ball mill or an oscillating mill. The inorganic halides may be dissolved in a solvent such as alcohol and precipitated as fine particles with a precipitating agent.

The carrier (E) may be clays, and the clays are usually mainly composed of clay minerals. The ion-exchange layered-compounds are compounds having a crystal structure wherein planes formed by ionic bonding or the like are piled on one another in parallel with a weak bond strength, and wherein the ions contained therein are exchangeable. Mast clay minerals are ion-exchange layered compounds. The clays, the clay minerals and the ion-exchange layered compounds are not limited to natural compounds but include synthetic products.

Examples of the ion-exchange layered compounds include those having layered crystal structures such as hexagonal closest packing structure, antimony structure, $CdCl_2$ structure and $CdI_2$ structure.

Examples of the clay minerals include kaolin, bentonite, kibushi clay, gairome clay, allophane, hisingerite, pyrophyllite, mica, montmorillonite, vermiculite, chlorite, palygorskite, kaolinite, nacrite, dickite and halloysite. Examples of the ion-exchange layered compounds include salts of polyvalent metals and crystalline acids such as $\alpha\text{-}Zr(HAsO_4)_2 \cdot H_2O$, $\alpha\text{-}Zr(HPO_4)_2$, $\alpha\text{-}Zr(KPO_4)_2 \cdot 3H_2O$, $\alpha\text{-}Ti(HPO_4)_2$, $\alpha\text{-}Ti(HAsO_4)_2 \cdot H_2O$, $\alpha\text{-}Sn(HPO_4)_2 \cdot H_2O$, $\gamma\text{-}Zr(HPO_4)_2$, $\gamma\text{-}Ti(HPO_4)_2$ and $\gamma\text{-}Ti(NH_4PO_4)_2 \cdot H_2O$.

The clays, the clay minerals and the ion-exchange layered compounds preferably have a pore volume, as measured on pores having a radius of not less than 20 Å by a mercury penetration method, of not less than 0.1 cc/g, and particularly preferably 0.3 to 5 cc/g. The pore volume is measured on pores having a radius of 20 to $3 \times 10^4$ Å by a mercury penetration method using a mercury porosimeter.

Achieving high polymerization activity tends to be difficult if the carrier has a pore volume of less than 0.1 cc/g as measured on pores having a radius of not less than 20 Å. It is also preferable that the clays and the clay minerals are subjected to chemical treatments.

Any chemical treatments, for example, a surface treatment to remove impurities on the surface and a treatment to modify the crystal structure of clay minerals, are employable. Examples of such chemical treatments include acid treatment, alkali treatment, salt treatment and organic substance treatment. The acid treatment removes impurities from the surface and also causes the elution of cations such as Al, Fe and Mg in the crystal structure to increase the surface area. The alkali treatment destroys the crystal structure of clay to bring about change in the structure of the clay. The salt treatment and the organic substance treatment produce, for example, ionic composites, molecular composites or organic derivatives to change the surface area or the interlayer distance.

The ion-exchange layered compound may be a layered compound in which the exchangeable ions between layers have been exchanged with other large and bulky ions utilizing ion exchange properties to enlarge the distance between the layers. The bulky ions play a pillar-like roll to support the layered structure and are generally called pillars. The introduction of other substances between layers of a layered compound is called intercalation. Examples of the guest compounds to be intercalated include cationic inorganic compounds such as $TiCl_4$ and $ZrCl_4$; metal alkoxides such as $Ti(OR)_4$, $Zr(OR)_4$, $PO(OR)_3$ and $B(OR)_3$ (R is a hydrocarbon group or the like); and metal hydroxide ions such as $[Al_{13}O_4(OH)_{24}]^{7+}$, $[Zr_4(OH)_{14}]^{2+}$ and $[Fe_3O(OCOCH_3)_6]^+$. These compounds are used singly, or two or more kinds are used in combination. The intercalation of the above compounds may be carried out in the presence of polymers obtained by hydrolysis of metal alkoxides such as $Si(OR)_4$, $Al(OR)_3$ and $Ge(OR)_4$ (R is a hydrocarbon group or the like) or in the presence of colloidal inorganic compounds such as $SiO_2$. Examples of the pillars include oxides produced by intercalation of the above metal hydroxide ions between layers followed by thermal dehydration.

The clays, the clay minerals and the ion-exchange layered compounds may be used as they are, or may be used after subjected to ball milling, sieving or the like. Moreover, they may be used after subjected to water adsorption or thermal dehydration treatment. Furthermore, they may be used singly, or two or more kinds may be used in combination.

Of these inorganic compounds, the clay minerals are preferable, and montmorillonite, vermiculite, hectorite, tenorite and synthetic mica are particularly preferable.

Examples of the organic compounds employable as the carrier (E) include granular or fine particulate solid compounds having a particle diameter of 10 to 300 μm. Such compounds include (co)polymers produced using α-olefins having 2 to 14 carbon atoms such as ethylene, propylene, 1-butene and 4-methyl-1-pentene as a main component, (co)polymers produced using vinylcyclohexane or styrene as a main component, and modified products of these polymers.

Organic Compound Component (F)

The organic compound component (F) is optionally used to improve catalytic performance. Examples of the organic compound include, but are not limited to, alcohols, phenolic compounds, carboxylic acids, phosphorus compounds and sulfonates.

As the alcohols, those represented by $R^{40}$—OH are usually employed. Here, $R^{40}$ is a hydrocarbon group having 1 to 50 carbon atoms, or a halogenated hydrocarbon group having 1 to 50 carbon atoms. Those represented by the above formula wherein $R^{40}$ is a halogenated hydrocarbon group are preferable.

As the phenolic compounds, those represented by $R^x$—OH are usually employed. Here, as $R^x$, those wherein the α,α'-position in the hydroxyl group is substituted with a hydrocarbon group having 1 to 20 carbon atoms are preferable.

As the carboxylic acids, those represented by $R^{41}$—COOH are usually employed. $R^{41}$ is a hydrocarbon group having 1 to 50 carbon atoms, or a halogenated hydrocarbon group having 1 to 50 carbon atoms, and particularly preferably a halogenated hydrocarbon group having 1 to 50 carbon atoms.

As preferred phosphorus compounds, phosphoric acids having a P—O—H bond, phosphates having a P—OR bond, and phosphine oxide compounds having a P=O bond are preferably employed. As the sulfonates, those represented by the following general formula (VIII) are employed.

[Chem. 37]

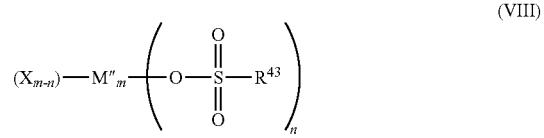

(VIII)

In the above formula, M'" is an element of Groups 1 to 14 of the periodic table; $R^{43}$ is a hydrogen atom, a hydrocarbon group having 1 to 20 carbon atoms, or a halogenated hydrocarbon group having 1 to 20 carbon atoms;

X is a hydrogen atom, a halogen atom, a hydrocarbon group having 1 to 20 carbon atoms, or a halogenated hydrocarbon group having 1 to 20 carbon atoms; m is an integer of 1 to 7; and n is an integer of 1 to 7.

Production Conditions of Organometallic Compound (1)

In the method for producing the organometallic compound (1) of the present invention, in the presence of the transition metal compound (A), the diene compound (B) and the organometallic compound (C), both of which are raw materials, are reacted with each other, optionally using the co-catalyst component (D), the carrier (F), and the organic compound component (F).

In the reaction, a solvent may be used or may not be used, but the reaction is performed preferably in a solution using an inert hydrocarbon solvent. Examples of employable inert hydrocarbon solvents include aliphatic hydrocarbons such as propane, butane, pentane, hexane, heptane, octane, decane, dodecane and kerosine; alicyclic hydrocarbons such as cyclopentane, cyclohexane and methylcyclopentane; aromatic hydrocarbons such as benzene, toluene, and xylene; halogenated hydrocarbons such as ethylene chloride, chlorobenzene and dichloromethane; and mixtures of these solvents.

The ratio of the diene compound (B) to the organometallic compound (C), both of which are raw materials, is such that the molar ratio [(B)/(C)] is generally in the range of 0.2 to 5, preferably 0.5 to 4, more preferably 0.6 to 3, still more preferably 0.8 to 2.

The transition metal compound (A) is used in such an amount relative to the diene compound (B) that the molar ratio [(A)/(B)] is generally in the range of 0.00001 to 1, preferably 0.0001 to 0.1, more preferably 0.001 to 0.05, still more preferably 0.005 to 0.03.

The usage amount of the co-catalyst component (D) is as follows. When the organometallic compound (D-1) is used, the amount thereof is such that the molar ratio [(D-1)/M'] of the component (D-1) to all transition metal atoms (M') in the transition metal compound (A) is generally in the range of 0.01 to 100000, and preferably 0.05 to 50000. When the organoaluminum oxy-compound (D-2) is used, the amount thereof is such that the molar ratio [(D-2)/M'] of the aluminum atom in the component (D-2) to the transition metal atom (M') in the transition metal compound (A) is generally in the range of 10 to 500000, and preferably 20 to 100000. When the ionized ionic compound (D-3) is used, the amount thereof is such that the molar ratio [(D-3)/M'] of the component (D-3) to the transition metal atom (M') in the transition metal compound (A) is generally in the range of 1 to 10, and preferably 1 to 5.

The usage amount of the organic compound component (F) is as follows. When the organometallic compound (D-1) is used as the co-catalyst component (D), the molar ratio [(F)/(D-1)] is generally in the range of 0.01 to 10, and preferably 0.1 to 5. When the organoaluminum oxy-compound (D-2) is used as the co-catalyst component (D), the molar ratio [(F)/(D-2)] is generally in the range of 0.001 to 2, and preferably 0.005 to 1. When the ionized ionic compound (D-3) is used as the component (D), the molar ratio [(F)/(D-3)] is generally in the range of 0.01 to 10, and preferably 0.1 to 5.

In the method of the present invention, the pressure in the reaction is not particularly limited, and any of normal pressure, reduced pressure and increased pressure is possible. The reaction is usually performed preferably under an inert gas atmosphere, but may be performed in the co-presence of hydrogen, as needed. If hydrogen is co-present, an organometallic compound (1) having a structure in which a hydrogen atom was added in place of R group or $R^{11}$ group of the organometallic compound (C) is generated. If hydrogen is used, the use thereof is such that the molar ratio [hydrogen/(C)] usually becomes 0.001 to 100, preferably 0.01 to 50. Hydrogen may be bubbled in a reaction solution. The pressure is not particularly limited, and any of normal pressure, reduced pressure and increased pressure is possible.

The temperature in the reaction between the diene compound (B) and the organometallic compound (C) is usually in the range of −80 to 100° C., preferably −30 to 60° C., particularly preferably −20 to 50° C. The reaction may be carried out in batchwise, semi-continuously, or continuously. The reaction time is usually 1 minute to 100 hours, preferably 5 minutes to 50 hours.

In the reaction, the transition metal compound (A), the diene compound (B), and the organometallic compound (C), the co-catalyst component (D), the carrier (E), and the organic compound component (F), which are optionally used, can be added and mixed in any order. For example, the diene compound (B), the carrier (E), the organic compound component (F), the organometallic compound (C), the co-catalyst component (D), and the transition metal compound (A) are added in this order.

The organometallic compound (1) of the present invention generated after the completion of the reaction can be purified, as needed, by methods such as filtration, recrystallization, distillation, and absorption. For example, a reaction mixture liquid is subjected to filtration in order to remove insolubles such as a carrier and a catalyst residue, and from the resultant, a solvent and a remaining organic compound are removed under reduced pressure. Then, the obtainable is dissolved again in a solvent, and the solution is subjected to cooling, recrystallization treatment, and the like.

In the reaction to produce the organometallic compound (1) of the present invention, the diene compound (B) and the organometallic compound (C), both of which are raw materials, are bonded to each other by an elementary reaction as represented by the following general formula (this formula typically shows a part involved with the reaction alone, and thus does not show the whole reaction.)

[Chem. 38]

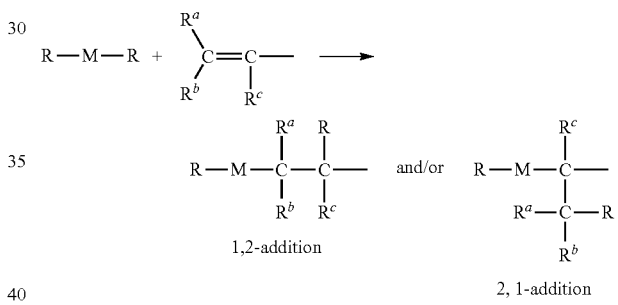

As shown in the above formula, the bonding forms include 1,2-addition and 2,1-addition. If the reaction between the diene compound (B) and the organometallic compound (C) has proceeded exclusively by 1,2-addition, the organometallic compound (1) generated is represented as shown in the following general formula (i). If the reaction between the diene compound (B) and the organometallic compound (C) has proceeded exclusively by 2,1-addition, the organometallic compound (1) generated is represented as shown in the following general formula (iii). If the reaction between the diene compound (B) and the organometallic compound (C) has proceeded by 1,2-addition and 2,1-addition, alternately, the organometallic compound (1) generated is represented as shown in the following general formula (ii).

[Chem. 39]

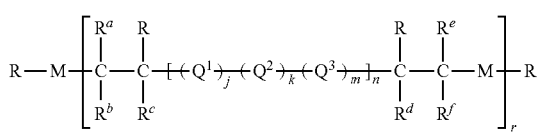

-continued

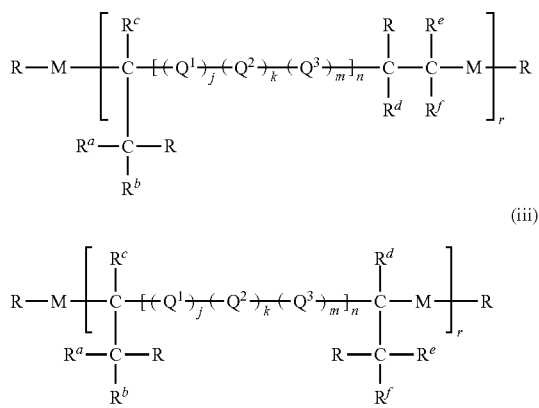

The corresponding relationships between the substituents in the above formulae (i) to (iii) and those in the general formula of the organometallic compound (1) are indicated in the following Table 1. As indicated in the table, h and p are each 1 in the occurrence of 1,2-addition, and are each 0 in the occurrence of 2,1-addition.

TABLE 1

| Formula (1) | $R^1$ | $R^2$ | $R^3$ | $R^4$ | $R^5$ | $R^6$ | $R^7$ | $R^8$ | $R^9$ | $R^{10}$ | h | p |
|---|---|---|---|---|---|---|---|---|---|---|---|---|
| Formula (i) | R | $R^a$ | $R^b$ | R | $R^c$ | R | $R^d$ | $R^e$ | $R^f$ | R | 1 | 1 |
| Formula (ii) | R | $R^c$ | $R^aR^bRC$- | — | — | R | $R^d$ | $R^e$ | $R^f$ | R | 0 | 1 |
| Formula (iii) | R | $R^c$ | $R^aR^bRC$- | — | — | — | — | $R^d$ | $R^eR^fRC$- | R | 0 | 0 |

The organometallic compound (1) of the present invention, if produced by the above method, is usually generated as a mixture of 1,2-addition and 2,1-addition. The proportion between 1,2-addition and 2,1-addition can be varied by changing types of the transition metal compound (A), the diene compound (B) and the organometallic compound (C) to be employed, the reaction conditions, and the like. Specifically, in general, increasing the reaction temperature lowers the proportion of 1,2-addition while decreasing the reaction temperature lowers the proportion of 2,1-addition, although this depends on the types of the transition metal compound (A), the diene compound (B), and the organometallic compound (C) to be employed.

The proportion between 1,2-addition and 2,1-addition can be calculated from a signal of carbon at α-position of a metal by $^{13}$C-NMR.

Alternatively, the proportion can be calculated from the structure change of the diene compound (B). Specifically, a mixture obtained of the organometallic compounds (i), (ii) and (iii) is reacted with water or an acid, to thereby convert a metal-carbon bond into a hydrogen-carbon bond. By analyzing the abundance ratio of an organic compound mixture obtained, the insertion proportion can be calculated. In particular, by previously grasping the retention times of the organic compounds corresponding to the organometallic compounds (i), (ii) and (iii), and carrying out the analysis using gas chromatograph, the ratio of the amounts of the organometallic compounds (i), (ii) and (iii) can be easily calculated, and from the value, the insertion proportions can be readily calculated.

The reaction to produce the organometallic compound (1) generates a chain compound and a cyclic compound. Typically, as shown in the following formulae, the reaction of the diene compound (B) with the organometallic compound (C) in an equimolar ratio results in the generation of such a cyclic compound as represented by (iv) or such a chain compound as represented by (v); the reaction involving an excessive of the diene compound (B) results in the generation of such a chain compound as represented by (vi); and the reaction involving an excessive of the organometallic compound (C) results in the generation of such a chain compound represented by (vii) (In the following general formulae, all of the bonding forms are 1,2-addition, but the above applies in the case of 2,1-addition, too.

[Chem. 40]

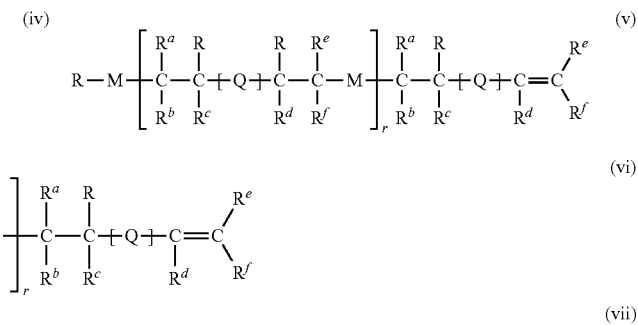

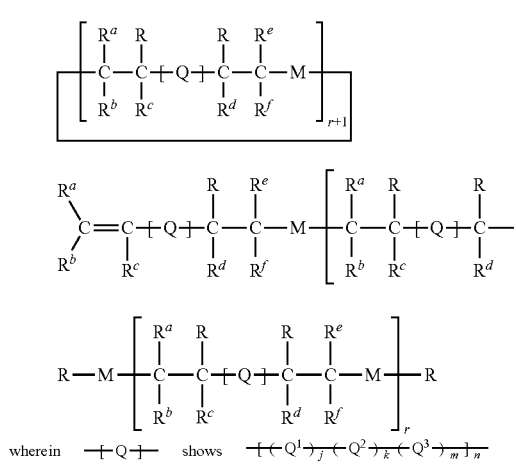

wherein $-\!\!+\!\!Q\!\!+\!\!-$ shows $-\!\!+\!\!(Q^1)_j\!\!+\!\!(Q^2)_k\!\!+\!\!(Q^3)_m\!\!+\!\!_n$ Provided that when d mol of the dine compound (B) is reacted with z mol of the organometallic compound (C), and the valence of the metal in the organometallic compound is defined as k, the number of r in the general formula, which is the number of an average repeating unit can be calculated as follows.

$$d > kz/2 > 0.5d: \qquad (1)$$

The chain compound represented by the general formula (vi) is generated, and the value of r can be calculated as follows:

$$r = [2d/(2d-kz)] - k$$

$$kz/2 > d: \qquad (2)$$

The chain compound represented by the general formula (vii) is generated, and the value of r can be calculated as follows:

$$r = 2d/(kz-2d)$$

When r obtained in the above relations is a number with a decimal point, the number is round off to a nearest integer.

The organometallic compound (1) of the present invention, if produced by the above method, is usually generated as a mixture of a chain compound and a cyclic compound.

[Use of Organometallic Compound (1)]

The organometallic compound (1) of the present invention can be used as a chain transfer agent, particularly as a reversible chain transfer agent in polymerization reaction of a double-bond containing compound, and is capable of producing a polymer having a carbon-metal bond at both terminals. By using the organometallic compound (1) of the present invention as a chain transfer agent, for example, in accordance with the methods as described in JP-A-2008-533277 and WO-2003-014046 pamphlet, a polymer is formally generated at the bond between carbon and metal of both terminals of the organometallic compound. As a result, even under the same condition, polymer with double molecular weight having a carbon-metal bond at both terminals can be obtained.

For example, the reaction between the organometallic compound (1) with linear or branched α-olefins having 2 to 30 carbon atoms, cyclic olefins, dienes, or polyenes, or aromatic vinyl compounds, can produce an organometallic compound (5) represented by the following general formula (5).

1-decene, 1-dodecene, 1-tetradecene, 1-hexadecene, 1-octadecene, 1-eicosene, vinylcyclopentane, vinylcyclohexane, allylcyclopentane, and allylcyclohexane;

cyclic olefins having 3 to 30 carbon atoms, preferably 3 to 20 carbon atoms, such as cyclopentene, cycloheptene, norbornene, 5-methyl-2-norbornene, tetracyclododecene, and 2-methyl-1,4,5,8-dimethano-1,2,3,4,4a,5,8,8a-octahydronaphthalene;

mono- or poly-alkyl styrenes, such as styrene, o-methylstyrene, m-methylstyrene, p-methylstyrene, o,p-dimethylstyrene, o-ethylstyrene, m-ethylstyrene, and p-ethylstyrene;

aromatic vinyl compounds such as 3-phenylpropylene, 4-phenylpropylene, and α-methylstyrene; and cyclic or chain dienes or polyenes having two or more double bonds having 4 to 30 carbon atoms, preferably 4 to 20 carbon atoms, such as butadiene, isoprene, 4-methyl-1,3-pentadiene, 1,3-pentadiene, 1,4-pentadiene, 1,5-hexadiene, 1,4-hexadiene, 1,3-hexadiene, 1,3-octadiene, 1,4-octadiene, 1,5-octadiene, 1,6-octadiene, 1,7-octadiene, ethylidene norbornene, vinyl norbornene, dicyclopentadiene, 7-methyl-1,6-octadiene, 4-ethylidene-8-methyl-1,7-nonadiene, and 5,9-dimethyl-1,4,8-decatriene.

The reaction between the organometallic compound (1) with the above diene or polyene can provide a polymer with branches at $A_x$, $A_y$, $A_z$, and $A_w$ of the general formula (5). Such a branched polymer is also included in the organometallic compound (5).

Of these compounds, more preferable are ethylene, propylene, 1-butene, 1-pentene, 3-methyl-1-butene, 1-hexene, 4-methyl-1-pentene, 3-methyl-1-pentene, 1-octene, 1-decene, vinylcyclohexane, norbornene, 5-methyl-2-norbornene, tetracyclododecene, butadiene, ethylidenenorbornene, vinylnorbornene, dicyclopentadiene, styrene, and p-methylstyrene.

These compounds can be employed singly or in combination of two or more kinds.

Furthermore, by performing functional group conversion by known methods at the carbon-metal bonds of the polymer having a carbon-metal bond at both terminals, a both-terminal-functional polymer, such as a both-terminal-functional polyolefin, can be produced. For example, by performing

[Chem. 41]

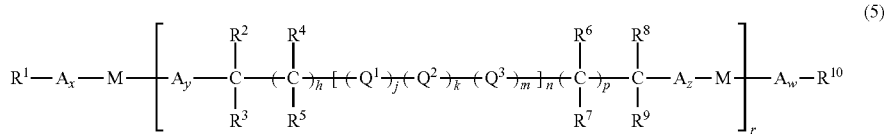

(5)

In the general formula (5), A is a unit derived from a linear or branched α-olefin having 2 to 30 carbon atoms, a cyclic olefin, a diene, a polyene, or an aromatic vinyl compound; x, y, z, and w are each an integer of 1 or more; x+y+z+w=8 to 100000.

M, $Q^1$, $Q^2$, $Q^3$, h, j, k, m, n, p, and $R^1$ to $R^{10}$ are defined in the same manner as in the general formula (1).

In the general formula (5), A is derived from a linear or branched α-olefin having 2 to 30 carbon atoms, a cyclic olefin, a diene, a polyene, or an aromatic vinyl compound.

Examples of such compounds include:

linear or branched α-olefins having 2 to 30 carbon atoms, preferably 2 to 20 carbon atoms, such as ethylene, propylene, 1-butene, 2-butene, 1-pentene, 3-methyl-1-butene, 1-hexene, 4-methyl-1-pentene, 3-methyl-1-pentene, 1-octene, functional group conversion at the carbon-metal bonds of the organometallic compound (5), a both-terminal-functional polymer can be produced.

Moreover, by using the functional groups introduced into both terminals as a polymerization initiator, or by using the functional groups that has been treated by known methods as a polymerization initiator and then by performing further polymerization, an ABA block polymer can be produced. Furthermore, by performing condensation polymerization using the functional groups introduced into both terminals as polymerization active sites, block polymers having various structures can be produced.

The organometallic compound (1) of the present invention can be used also as an organic synthesis reagent, a polymer material, or a precursor thereof, specifically as a nucleophilic reagent having plural active sites or a precursor thereof. In addition, by converting the metal moiety into a compound, a polymer with highly controlled structure or a precursor thereof is obtained.

EXAMPLES

Hereinafter, the present invention will be described with reference to Examples, but the present invention is not limited to these Examples. Analysis in Examples and Comparative Examples was carried out as follows.

[m1] NMR Measurement

NMR was measured employing NMR apparatus of 270 MHz or 500 MHz and deuterated benzene as a solvent (prepared after dehydration treatment using active molecular sieve under nitrogen atmosphere and purification by distillation under reduced pressure), unless otherwise noted. The analysis in $^1$H-NMR was based on residue protons of the deuterated solvent used as a solvent. The analysis in $^{13}$C-NMR was based on carbon of the deuterated solvent used as a solvent.

[m2] Gas Chromatograph (GC) Measurement

GC was measured under the following conditions.

<GC Measurement Conditions 1>
Apparatus: GC-2010 (manufactured by Shimadzu Corporation)
Column: DB-5MSUI (manufactured by Agilent Technologies)
  Inner diameter: 0.25 mm
  Length: 30 m
  Film thickness: 0.25 μm
Temperature:
  Column: held at 100° C. for 5 min, heated at a rate of 20° C./min, and then held at 300° C. for 10 min;
  Inlet: 300° C.
  Detector: 300° C.
Carrier gas: helium
  Initial flow rate: 1.10 mL/min
  Pressure set: 90 kPa
  Average linear velocity: 27.3 cm/sec
Sprit ratio: 30:1

<GC Measurement Conditions 2>
Apparatus: GC-2010 (manufactured by Shimadzu Corporation)
Column: DB-5MSUI (manufactured by Agilent Technologies)
  Inner diameter: 0.25 mm
  Length: 30 m
  Film thickness: 0.25 μm
Temperature:
  Column: held at 40° C. for 5 min, heated at a rate of 10° C./min, and then held at 300° C. for 10 min;
  Inlet: 300° C.
  Detector: 300° C.
Carrier gas: helium
  Initial flow rate: 1.10 mL/min
  Pressure set: 90 kPa
  Average linear velocity: 27.3 cm/sec
Sprit ratio: 30:1

[m3] Gas Chromatography Mass Analysis (FC-MS)

GC-MS was measured under the following conditions.

<GC-MS Measurement Conditions 1>
Apparatus: GCMS-QP5050A (manufactured by Shimadzu Corporation)
Column: DB-1 (manufactured by Agilent Technologies)
  Inner diameter: 0.25 mm
  Length: 30 m
  Film thickness: 0.25 μm
Temperature:
  Column: held at 100° C. for 5 min, heated at a rate of 20° C./min, and then held at 200° C. for 10 min
  Inlet: 300° C.
  Detector: 300° C.
Carrier gas: helium
  Initial flow rate: 1.8 mL/min
  Pressure Set: 104.8 kPa
  Average linear velocity: 48.5 cm/sec
Sprit ratio: 10:1

<GC-MS Measurement Conditions 2>
Apparatus: GCMS-QP5050A (manufactured by Shimadzu Corporation)
Column: DB-1 (manufactured by Agilent Technologies)
  Inner diameter: 0.25 mm
  Length: 30 m
  Film thickness: 0.25 μm
Temperature:
  Column: held at 40° C. for 5 min, heated at a rate of 10° C./min, and then held at 300° C. for 10 min;
  Inlet: 300° C.
  Detector: 300° C.
Carrier gas: helium,
  Initial flow rate: 1.7 mL/min
  Pressure set: 100.0 kPa
  Average linear velocity: 47.4 cm/sec
Sprit ratio: 10:1

[m4] Gel Permeation Chromatography (GPC)

GPC was measured under the following conditions.

<GPC Measurement Conditions>
Measurement apparatus: gel permeation chromatograph Alliance GPC-2000 (manufactured by Waters)
Analysis apparatus: data processing soft, Empower 2 (manufactured by Waters)
Column: TSKgel GMH$_6$-HT×2+TSKgel GMH$_6$-HTL×2, each of which is 7.5 mm I.D.×30 cm (manufactured by Tosoh Corporation)
Column temperature: 140'C
Mobile phase: o-dichlorobenzene (containing 0.025% of BHT)
Detector: differential refractive index detector
Flow rate: 1 mL/min
Sample concentration: 0.15% (w/v)
Column calibration: monodisperse polystyrene (manufactured by Tosoh Corporation)

The following catalysts and co-catalyst were used.

"Catalyst 1" is bis-(1-(2-methylcyclohexyl)(2-oxoyl-3,5-di(t-butyl)phenylimino)) zirconiumdimethyl, having the following structure.

[Chem. 42]

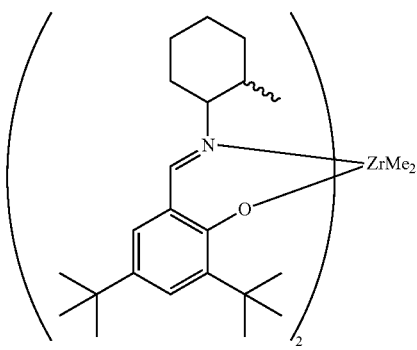

"Catalyst 2" is [N-(2,6-diisopropylphenyl)amido(2-isopropylphenyl)(α-naphthalene-2-diyl(6-pyridine-2-diyl)methane)]hafniumdimethyl, having the following structure.

[Chem. 43]

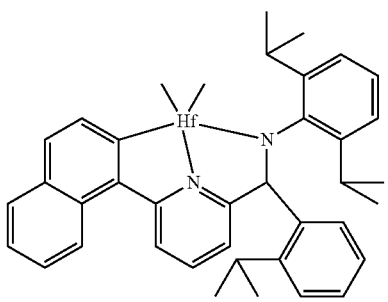

"Co-catalyst 1" is triphenylcarbeniumtetrakis(pentafluorophenyl)borate.

Example 1

Synthesis of Compound X-1

A 50 mL two-neck recovery flask with a stirrer having a three-way cock connected was sufficiently dried under dried nitrogen, and thereto, at room temperature, 7.5 mL of n-hexane, 2.0 mL (0.20 mmol in terms of an aluminum atom) of 0.1 M n-hexane solution of methylaluminoxane, 2.0 mL (2.0 mmol in terms of 1,9-decadiene) of 1.0 M n-hexane solution of 1,9-decadiene, and 3.0 mL (3.0 mmol in terms of a zinc atom) of 1.0 M n-hexane solution of diethylzinc were added. The reaction mixture liquid was cooled to 0° C., and with stirring, 0.5 mL (40 μmol in terms of mol) of 0.08 M toluene solution of the Co-catalyst 1 was added thereto. Then, thereto was added 2.0 mL (20 μmol in terms of mol) of a catalyst solution separately prepared from the catalyst 1 (60.6 mg, 77.9 μmol) and 7.8 mL of cyclohexane. The solution immediately showed orange color. The solution was stirred at 0° C. for 1 hour with light shield, to thereby obtain an orange mixture. A part of the mixture was sampled under inert atmosphere, and the sample was concentrated under reduced pressure, to thereby obtain a yellow viscous mixture.

Approximately 30 mg of this yellow viscous mixture was dissolved in approximately 0.5 mL of deuterated benzene, thereby preparing a sample for NMR.

By $^1$H-NMR, signals of α-position of zinc broadened at −0.2 to 0.8 ppm, and signals of hydrocarbons broadened at 0.8 ppm to 2.0 ppm were observed. No signals were observed in olefin regions. $^1$H-NMR spectrum is shown in FIG. 1.

By $^{13}$C-NMR, signals of α-position of zinc broadened at 23 to 24 ppm were observed. This value shows good correlation with a signal of α-position of zinc indicated in J. Organomet. Chem. 1982, 224, 217-221.

Into this NMR sample solution, distilled water was added under nitrogen atmosphere. Then, the mixture was sufficiently stirred to react zinc with water, thereby converting a carbon-zinc bond into a carbon-hydrogen bond. Thereafter, a solid matter precipitated was removed by cotton filtration. Then, an organic layer separated was analyzed under GC measurement conditions 1, thereby indirectly observing the structure of the product.

As a result, a peak of 1,9-decadiene, a raw material, was not observed. A peak of 3,10-dimethyldodecane, obtainable by 1,2-addition of diethylzinc occurring at two olefin sites, was observed at a retention time of 8.5 minutes. A peak of 3-methyltridecane, obtainable by 1,2-addition and 2,1-addition of diethylzinc occurring at one olefin site and at the other olefin site, respectively, was observed at a retention time of 8.8 minutes. The ratio of the areas of these two peaks was 92:8. A peak of tetradecane, obtainable by 2,1-addition of diethylzinc occurring at two olefin sites, was not detected. The correlations between retention times and the compounds were analyzed under GC-MS measurement conditions 1.

From the above result, it was found that the organometallic compound generated was a compound (X-1) wherein r=2 in the following formula, and s:t:u=92:8:0.

[Chem. 44]

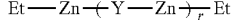

(Compound X-1)

wherein Y is a structure represented by $Y_1$, $Y_2$, or $Y_3$, shown below, and the proportion of $Y_1$:$Y_2$:$Y_3$=s:t:u (molar ratio).

[Chem. 45]

$Y_1$:

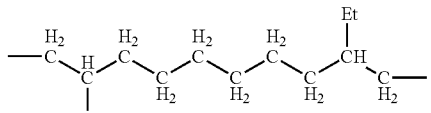

$Y_2$:

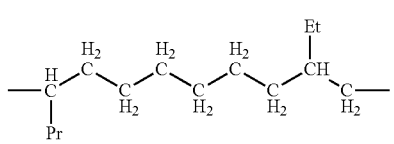

$Y_3$:

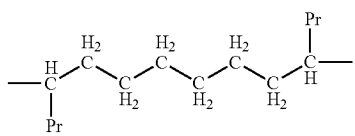

Example 2

Synthesis of Compound X-1

The same procedure was carried out as in Example 1, except that the temperature at which the Co-catalyst 1 and the Catalyst 1 were added was changed to room temperature, thereby obtaining a yellow mixture. A part of the mixture was sampled under inert atmosphere, and the sample was concentrated under reduced pressure, to thereby obtain a yellow viscous mixture.

A part of this yellow viscous mixture was sampled, and into the sample, hexane and distilled water were added under the nitrogen atmosphere. Then, the mixture was sufficiently stirred to react zinc and water, thereby converting a carbon-zinc bond to a carbon-hydrogen bond. Thereafter, a solid matter precipitated was removed by cotton filtration. Then, an organic layer separated was analyzed under GC measurement conditions 1, thereby indirectly observing the structure of the product.

As a result, a peak of 1,9-decadiene, a raw material, was not observed. A peak of 3,10-dimethyldodecane, obtainable by 1,2-addition of diethylzinc occurring at two olefin sites, was observed at a retention time of 8.5 minutes. 3-methyltridecane, obtainable by 1,2-addition and 2,1-addition of diethylzinc occurring at one olefin site and the other olefin site, respectively, was observed at a retention time of 8.8 minutes. A peak of tetradecane, obtainable by 2,1-addition of diethylzinc occurring at two olefin sites, was detected at a retention time of 9.1 minutes. The correlations between retention times and compounds were analyzed under GC-MS measurement conditions 1.

From the above result, it was found that the organometallic compound generated was a compound (X-1) wherein r=2 in the above formula described in Example 1, and s:t:u=76:22:2.

Example 3

Synthesis of Compound X-3

A 100 mL two-neck recovery flask with a stirrer having a three-way cock connected was sufficiently dried under dried nitrogen, and thereto, at room temperature, 9.1 mL (49.4 mmol) of 1,9-decadiene, 50.0 mL (54.5 mmol in terms of a zinc atom) of 1.09 M n-hexane solution of diethylzinc, and 1.0 mL (0.10 mmol in terms of an aluminum atom) of 0.1 M n-hexane solution of methylaluminoxane were added. Further, 7.0 mL (560 μmol in terms of mol) of 0.08 M toluene solution of the Co-catalyst 1 was added, and then, 27.0 mL (270 μmol in terms of mol) of 0.01 M cyclohexane solution of the Catalyst 1 was added. The solution immediately showed deep orange color. The solution was stirred for 1 hour with light shielded, thereby obtaining an orange mixture.

A part of this orange mixture was sampled, and into the sample, isobutyl alcohol was added under nitrogen atmosphere. Then, the mixture was sufficiently stirred, and hydrochloric acid was added thereto to thereby dissolve a precipitated matter. Then, an organic layer separated was analyzed under GC measurement conditions 1, thereby indirectly observing the structure of the product. As a result, it was found that the organometallic compound generated was a compound (X-3) wherein r=9 in the above formula described in Example 1, and s:t:u=76:22:2.

Example 4

Synthesis of Compound X-4

A 200 mL two-neck recovery flask with a stirrer having a three-way cock connected was sufficiently dried under dried nitrogen, and thereto, at room temperature, 7.4 mL (40.2 mmol) of 1,9-decadiene, and 28.0 mL (28.0 mmol in terms of an aluminum atom) of 1.0 M n-decane solution of triethylaluminum were added. Further, 5.0 mL (0.4 mmol in terms of mol) of 0.08 M toluene solution of the Co-catalyst 1 was added, and then, 20.0 mL (0.2 mmol in terms of mol) of 0.01 M cyclohexane solution of the Catalyst 1 was added. The solution immediately showed deep yellow color. The solution was stirred for 1 hour with light shielded, thereby obtaining a yellow mixture.

A part of this orange mixture was sampled, and into the sample, isobutyl alcohol was added under nitrogen atmosphere. Then, the mixture was sufficiently stirred, and hydrochloric acid was added, and then the mixture was cotton-filtered. Then, an organic layer separated was analyzed under GC measurement conditions 1, thereby indirectly observing the structure of the product. As a result, it was found that the organometallic compound generated was a compound (X-4) wherein r+m=22 in the following formula, and s:t:u=90:9:1.

[Chem. 46]

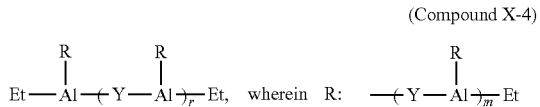

(Compound X-4)

wherein Y is a structure represented by $Y_1$, $Y_2$, or $Y_3$, shown below, and the proportion of $Y_1$:$Y_2$:$Y_3$=s:t:u (molar ratio).

[Chem. 47]

$Y_1$:

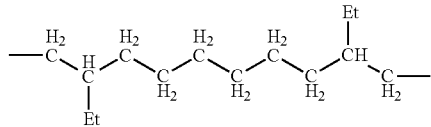

$Y_2$:

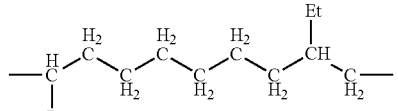

$Y_3$:

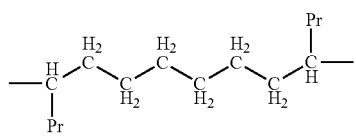

Example 5

Synthesis of Compound X-5

Synthesis of Compound X-5-1

Into a 100 mL two-neck recovery flask with a stirrer having a three-way cock and a dropping funnel connected, at room temperature, 3.50 g (40.6 mmol) of 4-pentene-1-ol, 4.21 g (41.6 mmol) of triethylamine, and 30 mL of hexane were introduced. With stirring, a hexane solution (10 mL) of 5.02 g (19.8 mmol) of diphenyl dichlorosilane was dropped over 5 minutes. At room temperature, the mixture was stirred for 1 hour, and then cooled to 0° C. Then, the reaction was terminated by adding 5 mL of a saturated sodium hydrogen carbonate aqueous solution. Into the reaction liquid, hexane and water were added, and an organic layer was separated. Then, the organic layer was washed using a saturated sodium hydrogen carbonate aqueous solution. The organic layer was concentrated and sufficiently dried under reduced pressure, thereby obtaining 2.12 g of a transparent viscous liquid. This transparent viscous liquid was found by $^1$H-NMR using deuterated chloroform solvent to be a compound X-5-1 represented by the following formula.

[Chem. 48]

(Compound X-5-1)

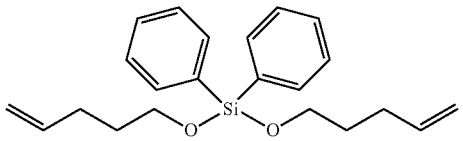

Synthesis of Compound X-5

The same procedure was carried out as in Example 2, except that 1,9-decadiene was replaced with the Compound X-5-1, thereby obtaining a yellow mixture. A part of this yellow mixture was sampled under inert atmosphere, and into the sample, isobutyl alcohol was added. Then, the mixture was sufficiently stirred and hydrochloric acid was added thereto to thereby dissolve a precipitated matter. Then, an organic layer separated was analyzed under GC measurement conditions 2, thereby indirectly observing the structure of the product. As a result, a peak of 4-methyl-1-hexenol, obtainable by 1,2-addition of diethylzinc occurring at an olefin site of the Compound X-5-1 and then the decomposition of a silyl-oxygen moiety, was observed at a retention time of 9.6 minutes. A peak of 1-heptanol, obtainable by 2,1-addition of diethylzinc occurring at an olefin site of the Compound X-5-1 and then the decomposition of a silyl-oxygen moiety, was observed at a retention time of 10.1 minutes. The ratio of the areas of these two peaks was 95:5. The correlations between retention times and the compounds were analyzed under GC-MS measurement conditions 2. From the above result, it was found that the organometallic compound generated was a compound (X-5) wherein r=2 in the following formula, and s:t:u=90:9:1.

[Chem. 49]

(Compound X-5)

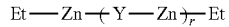

wherein Y is a structure represented by $Y_1$, $Y_2$, or $Y_3$, shown below, and the proportion of $Y_1:Y_2:Y_3=r:p:q$ (molar ratio).

[Chem. 50]

$Y_1$:

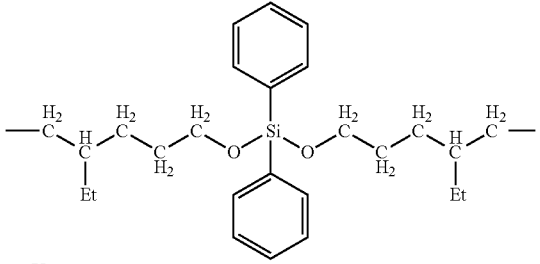

$Y_2$:

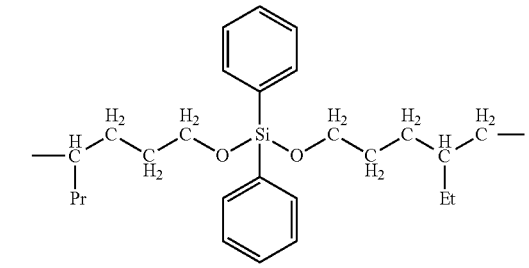

$Y_3$:

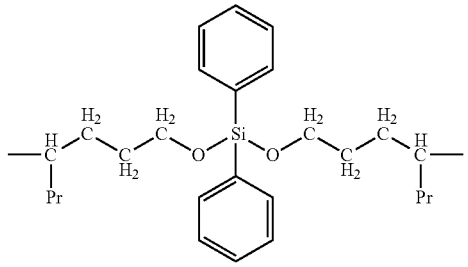

Example 6

Synthesis of Compound X-6

A 30 mL two-neck recovery flask with a stirrer having a three-way cock connected was sufficiently dried under dried nitrogen, and thereto, at room temperature, 8.0 mL of n-hexane, 0.2 mL (0.04 mmol in terms of an aluminum atom) of 0.2 M n-hexane solution of methylaluminoxane, 0.64 mL (4.3 mmol in terms of mol) of 1,7-octadiene, and 3.7 mL (4.0 mmol in terms of a zinc atom) of 1.09 M n-hexane solution of diethylzinc were added. While the reaction mixture liquid was stirred at room temperature, 0.5 mL (0.04 mmol in terms of mol) of 0.08 M toluene solution of the Co-catalyst 1 was added thereto. And, thereto was added 2.0 mL (20 μmol in terms of mol) of a catalyst solution separately prepared from the catalyst 1 (60.6 mg, 77.9 μmol) and 7.8 mL of cyclohexane. The solution immediately showed orange color. The solution was stirred at room temperature for 1 hour with light shield, and concentrated under reduced pressure, to thereby obtain an orange viscous mixture. A part of this orange viscous mixture was sampled under inert atmosphere, and into the sample, 1.0 M hydrochloric acid was added, and the mixture was sufficiently stirred, thereby converting a carbon-zinc bond into a carbon-hydrogen bond. Then, an organic layer separated was analyzed under GC measurement conditions 2, thereby indirectly observing the structure of the product.

As a result, a peak of 1,7-octadiene, a raw material, was not observed. A peak of 7-methyl-1-nonene, obtainable by 1,2-addition of diethylzinc occurring at one olefin site, was observed at a retention time of 10.6 minutes. A peak of 1-dodecene, obtainable by 2,1-addition of diethylzinc occurring at one olefin site, was observed at a retention time of 11.0 minutes. A peak of 3,8-dimethyldecane, obtainable by 1,2-addition of diethylzinc occurring at two olefin sites, was observed at a retention time of 13.3 minutes. A peak of 3-methylundecane, obtainable by 1,2-addition and 2,1-addition of diethylzinc occurring at one olefin site and the other olefin site, respectively, was observed at a retention time of 13.7 minutes. A peak of dodecane, obtainable by 2,1-addition of diethylzinc occurring at two olefin sites, was observed at a retention time of 14.2 minutes. The ratio of the areas of these five peaks was 11:2:72:13:1. The correlations between retention times and the compounds were analyzed under GC-MS measurement conditions 2. From the above result, it was found that the organometallic compound generated was a compound (X-6) wherein r=12 in the following formula, and s:t:u=84:15:1, and v:w=84:16.

[Chem. 51]

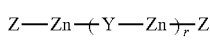

(Compound X-6)

wherein Y is a structure represented by $Y_1$, $Y_2$, or $Y_3$, shown below, and Z is a structure represented by $Z_1$ or $Z_2$, shown below; and the proportion of $Y_1:Y_2:Y_3$=s:t:u (molar ratio), and the proportion of $Z_1:Z_2$=v:w (molar ratio).

[Chem. 52]

$Y_1$:

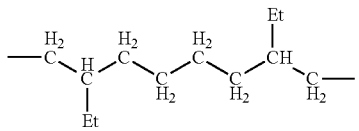

$Y_2$:

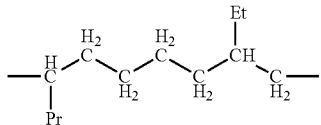

$Y_3$:

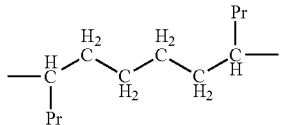

$Z_1$:

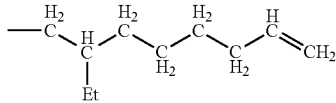

$Z_2$:

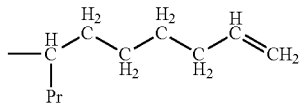

Example 7

Synthesis of Compound X-7

Preparation of Solid Component A

Under nitrogen flow, 30 g of silica (manufactured by Asahi Glass Co., Ltd., specific surface area: 870 m$^2$/g, pore volume: 0.8 mL/g, average particle diameter: 11.9 μm) which had been dried at 150° C. for 5 hours was suspended with 466 mL of purified toluene. Then, into the suspension, 134.3 mL of methylaluminoxane (manufactured by Albemarle Corporation, 20% toluene solution, 308 mmol in terms of an Al atom) was dropped at 1 to 5'C for 30 minutes. Then, the mixture was heated over 1.5 hours, and reacted at 95'C for 4 hours. The temperature of the reaction liquid was decreased to 60° C., and a supernatant liquid was removed by decantation method. A solid component A thus obtained (the carrier (E)) was washed three times using purified toluene. Then, toluene was added thereto, thereby preparing a toluene slurry of the solid component A. A part of the solid component A obtained was collected to study the concentration. It was found that the slurry concentration was 0.1189 g/mL, and Al concentration was 0.8377 mmol/mL.

Preparation of Solid Catalyst Component B

Into a 200 mL glass flask replaced with nitrogen, 45.2 mL of purified toluene, and 44.8 mL (37.5 mmol in terms of an Al atom) of the toluene slurry of the solid component A prepared above were introduced. Then, with stirring, 0.0075 mmol/mL toluene solution (10 mL) of the Catalyst 1 was dropped over 5 minutes, and stirred for 1 hour at room temperature. Then, a supernatant liquid was removed by decantation method, and the residue was washed three times using 50 mL of toluene. Then, 50 mL of toluene was added thereto, thereby preparing a toluene slurry of a solid catalyst component B. A part of the toluene slurry of the solid component B obtained was collected to study the concentration. It was found that Zr concentration was 0.001381 mmol/mL, and Al concentration was 0.6745 mmol/mL.

Synthesis of Compound X-7

A 30 mL Schlenk flask with a stirrer having a three-way cock connected was sufficiently dried under dried nitrogen, and thereto, at room temperature, 5 mL of toluene, 0.13 mL (0.20 mmol in terms of an aluminum atom) of 1.5 M n-toluene solution of methylaluminoxane, 0.29 mL (1.9 mmol in terms of mol) of 1,7-octadiene, and 1.9 mL (0.20 mmol in terms of a zinc atom) of 1.05 M n-hexane solution of diethylzinc were added. While the mixture liquid was stirred at room temperature, 0.5 mL (0.04 mmol in terms of mol) of 0.08 M hexane solution of the Co-catalyst 1 was added thereto. And, thereto was added the solid catalyst component B (16.5 mL (0.02 mmol in terms of a zirconium atom) of 1.38 mM toluene slurry). The solution was stirred at room temperature for 20 hours with light shield.

Under inert atmosphere, a part of the reaction liquid was sampled. By reacting isobutyl alcohol with the organic zinc, a carbon-zinc bond was converted to a carbon-hydrogen bond, and an organic layer separated after adding n-hexane was analyzed under GC measurement conditions 2, thereby indirectly observing the structure of the product. As a result, a peak of 1,7-octadiene, a raw material, was not observed. A peak of 3,8-dimethyldecane, obtainable by 1,2-addition of diethylzinc occurring at two olefin sites, was observed at a retention time of 13.3 minutes. A peak of 3-methylundecane, obtainable by 1,2-addition and 2,1-addition of diethylzinc occurring at one olefin site and the other olefin site, respectively, was observed at a retention time of 13.7 minutes. A peak of dodecane, obtainable by 2,1-addition of diethylzinc occurring at two olefin sites, was detected at a retention time of 14.2 minutes. The ratio of the areas of these three peaks was 84:15:1. The correlations between retention times and compounds were analyzed under GC-MS measurement conditions 2. From the above result, it was found that the organometallic compound generated was a compound (X-7) wherein r=32 in the following formula, and s:t:u=85:14:1.

The slurry obtained was allowed to stand still for 5 minutes, and a supernatant liquid was sampled, and the sample was analyzed by ICP emission method. It was found that the zinc concentration was 0.046 M, and the zirconium concentration was less than 0.055 mM. The ratio of the zirconium concentration to the zinc concentration was less than 0.0012. Thus, an organozinc compound solution having an extremely low zirconium concentration was obtained.

[Chem. 53]

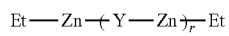

(Compound X-7)

wherein Y is a structure represented by $Y_1$, $Y_2$, or $Y_3$, shown below, and the proportion of $Y_1:Y_2:Y_3=r:p:q$ (molar ratio).

[Chem. 54]

$Y_1$:

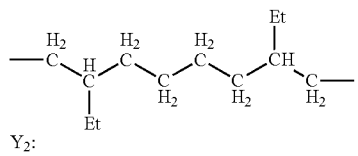

$Y_2$:

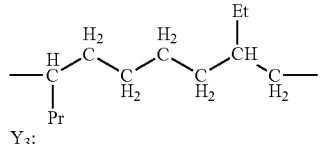

$Y_3$:

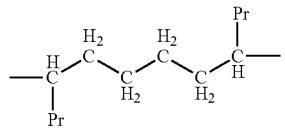

Example 8

Into a stainless (SUS) autoclave sufficiently dried with dried nitrogen, 50 mL of n-hexane was introduced. Pressurization to 0.5 MPa using ethylene followed by the discharge of the pressure to normal pressure was repeated three times, thereby saturating a liquid layer and a gas layer with ethylene. With stirring, the temperature was increased to 120° C., and then ethylene was further added, thereby pressurizing to 0.7 MPa. Then, 0.2 mmol in terms of an aluminum atom of methylaluminoxane (MMAO), 0.24 mmol in terms of a zinc atom of the yellow mixture obtained in Example 2, and 4.0 µmol in terms of mol of the Co-catalyst 1 (0.08 M toluene solution) were added. Then, 1.0 µmol in terms of mol of the Catalyst 1 (0.33 M toluene solution) was added, thereby initiating polymerization. During the polymerization, ethylene was added so that the pressure would be always 0.7 MPa. The reaction was made at 120° C. for 10 minutes, and 5 mL of isobutyl alcohol was added to terminate the polymerization. After the completion of the polymerization, the reaction product was pored into methanol to precipitate a whole amount of the polymer. Then, hydrochloric acid was added, and filtration using a glass filter was carried out. The polymer was dried under reduced pressure at 80° C. for 10 hours, and then 1.44 g of the polymer was obtained. The polymerization activity was 8600 g/mmol-Zr·hr. The molecular weight was measured by GPC, and it was found that in terms of polyethylene, the number average molecular weight (Mn) was 1990, the weight average molecular weight (Mw) was 3530, and Mw/Mn was 1.78.

This polymer was dissolved in deuterated orthodichlorobenzene, and the solution was measured by $^1$H-NMR and $^{13}$C-NMR. From a signal of $^{13}$C-NMR obtained, the terminal carbon and the amount of branches were measured. It was found that per 1000 carbons, a methyl branch was not observed, an ethyl branch was observed in an amount of 2.4, and a propyl branch was observed in an amount of 0.3. This result indicates that a polymer in which ethylene was inserted into a carbon-zinc bond of the Compound X-2 was obtained. Namely, this result demonstrates that the Compound X-2 functions as a chain transfer agent.

Example 9

Into a 500 mL glass reactor sufficiently dried under dried nitrogen, 250 mL of decane was introduced. After the temperature was increased to 100° C., with stirring, ethylene gas of normal pressure (flow rate: 100 L/hr) was blown into the reactor. While ethylene gas was blown, 0.20 mmol in terms of an aluminum atom of methylaluminoxane (MAO), 4.02 mmol in terms of a zinc atom of the orange mixture obtained in Example 3, and 16.0 µmol in terms of mol of the Co-catalyst 1 (0.08 M toluene solution) were added. Then, 4.0 µmol in terms of mol of the Catalyst 1 (0.001 M toluene solution) was added, thereby initiating polymerization. The reaction was made at 100° C. for 10 minutes, and then the blowing of ethylene gas was terminated. Instead, while nitrogen (flow rate: 50 L/hr) was blown, 3.4 mL (23.9 mmol) of ethylsuccinylchloride was introduced, and stirred at 100° C. Five minutes thereafter, a white precipitate was observed. Ten minutes thereafter, with cooling, 3.0 mL of pure water was added, thereby terminating the reaction. The temperature was cooled to room temperature, and then the reaction product was poured into a mixed solution of acetone (0.5 L) and methanol (0.5 L) to precipitate a polymer. The polymer was collected by filtration. The polymer was dried under reduced pressure at 100° C. for 12 hours. 9.87 g of the polymer was obtained.

Figure 2:
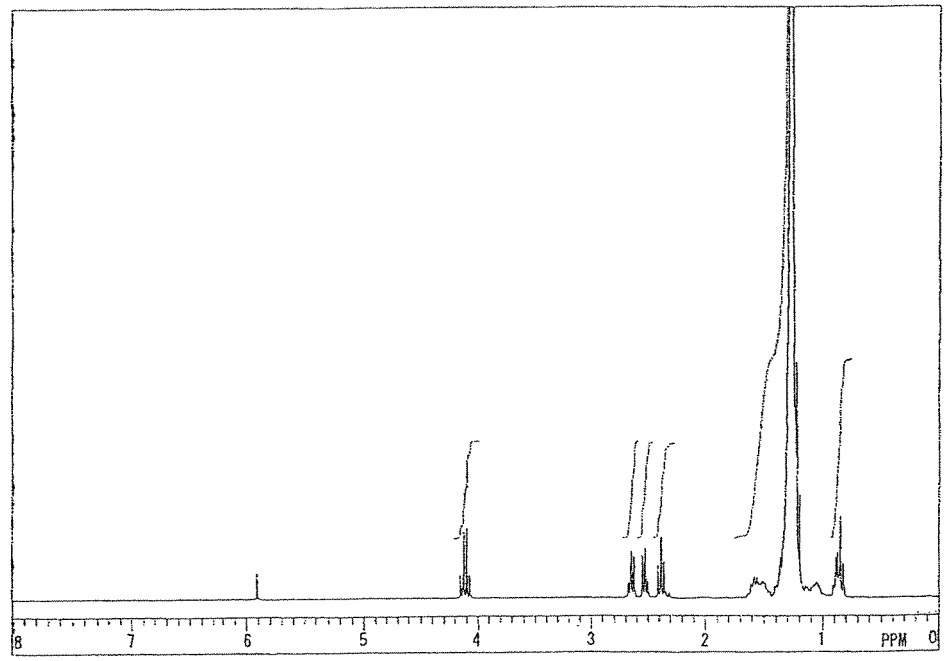
FIG. 2 is a $^1$H-NMR spectrum of a polymer obtained in Example 9.

This polymer was dissolved in deuterated tetrachloroethane, and the solution was subjected to measurement by $^1$H-NMR. $^1$H-NMR spectrum is shown in FIG. 2. In this spectrum, a quartet corresponding to methylene group of ethylester was observed at around 4.1 ppm; a peak corresponding to methylene group of β-position of ethylester was observed at around 2.7 ppm; a peak corresponding to methylene group of α-position of ethylester was observed at around 2.5 ppm; a peak corresponding to methylene group of δ-position of ethylester was observed at around 2.3 ppm; and a peak corresponding to a terminal methyl and a methyl group derived from an ethyl branch was observed at around 0.8 ppm. The ratio of the sum of integrated values of the peaks at around 4.1 ppm, at around 2.7 ppm, at around 2.5 ppm, and at around 2.3 ppm to an integrated value of the peak at around 0.8 ppm was 8: 3.76. Thus, it was found that a both-terminal-functional polyethylene was obtained in which the ratio (functionalized terminal ratio) of the number of functional groups present at terminals to the total number of terminals of the polymer was 82%.

Example 10

Into a 500 mL glass reactor sufficiently dried under dried nitrogen, 250 mL of toluene was introduced. After the temperature was increased to 50° C., with stirring, ethylene gas of normal pressure (flow rate: 100 L/hr) and propylene gas of normal pressure (flow rate: 100 L/hr) were blown into the reactor. While these gases were blown, 0.20 mmol in terms of an aluminum atom of methylaluminoxane (MMAO), 4.01 mmol in terms of a zinc atom of the organozinc compound solution obtained in Example 7, and 16.0 µmol in terms of mol of the Co-catalyst 1 (0.08 M toluene solution) were added. Then, 4.0 µmol in terms of mol of the Catalyst 2 (0.001 M toluene solution) was added, thereby initiating polymerization. The reaction was made at 50° C. for 2 minutes, and then the blowing of the gases was terminated. Instead, while nitrogen (flow rate: 50 L/hr) was blown, 3.4 mL (23.5 mmol) of ethylsuccinylchloride was introduced, and stirred at 50° C. Ten minutes thereafter, with cooling, 3.0 mL of pure water was added, thereby terminating the reaction. The temperature was cooled to room temperature, and then the reaction product was poured into pure water (1.0 L). Using a separating funnel, an organic layer was separated, and the organic layer was washed using a sodium hydrogen carbonate aqueous solution, and further washed using pure water. The resultant organic layer was concentrated, thereby obtaining a liquid polymer. This polymer was dried under reduced pressure at 100° C. for 12 hours. 2.96 g of the polymer was obtained.

Figure 3:
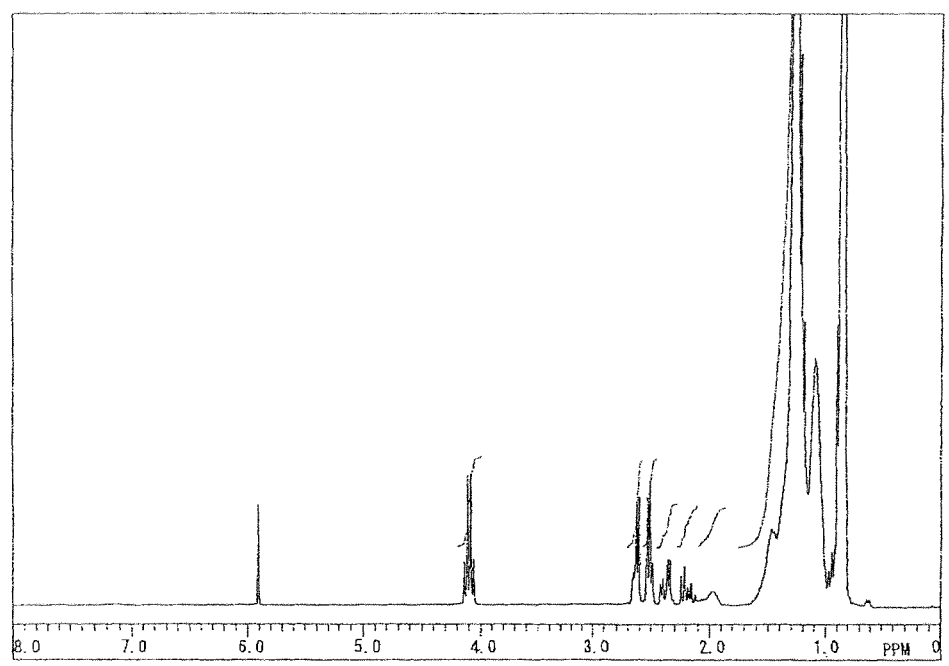
FIG. 3 is a $^1$H-NMR spectrum of a polymer obtained in Example 10.

This polymer was dissolved in deuterated tetrachloroethane, and the solution was subjected to measurement by $^1$H-NMR, $^1$H-NMR spectrum is shown in FIG. 3. In this spectrum, a quartet corresponding to methylene group of ethylester was observed at around 4.1 ppm; a peak corresponding to methylene group of β-position of ethylester was observed at around 2.7 ppm; a peak corresponding to methylene group of α-position of ethylester was observed at around 2.5 ppm; and a peak corresponding to methylene group of δ-position of ethylester was observed at around 2.1 ppm to 2.4 ppm. It was found from this that a both-terminal-functional ethylene propylene copolymer having ethylester at the terminals was obtained.

Example 11

Into a 500 mL glass reactor sufficiently dried under dried nitrogen, 250 mL of toluene, and 15 mL of 1-octene were introduced. After the temperature was increased to 50° C., with stirring, ethylene gas of normal pressure (flow rate: 100 L/hr) was blown into the reactor. While ethylene gas was blown, 0.20 mmol in terms of an aluminum atom of methylaluminoxane (MMAO), 2.0 mmol in terms of a zinc atom of the organozinc compound solution obtained in Example 7, and 16.0 µmol in terms of mol of the Co-catalyst 1 (0.08 M toluene solution) were added. Then, 0.25 µmol in terms of mol of the Catalyst 2 (0.001 M toluene solution) was added, thereby initiating polymerization. The reaction was made at 50° C. for 10 minutes, and then 0.05 mmol in terms of mol of bis(1,5-cyclooctadiene)nickel (0.01 M toluene solution) was added. While keeping the blowing of the ethylene gas, stirring at room temperature was carried out. Two hours thereafter, the reaction product was poured into a mixed solution of methanol (1.0 L) and concentrated hydrochloric acid (3 mL) to precipitate a polymer. The polymer was collected by filtration. This polymer was dried under reduced pressure at 100° C. for 12 hours. 1.5 g of a white viscous polymer was obtained.

This polymer was dissolved in deuterated toluene, and the solution was subjected to measurement by $^1$H-NMR. In this spectrum, a peak corresponding to methine group of a terminal olefin was observed at around 5.8 ppm; and a peak corresponding to methylene group of a terminal olefin was observed at around 5.0 ppm. It was found from this that this polymer had an olefin at the terminals.

Reference Example 1

The same procedure as in Example 7 was carried out, except that in Example 7, the yellow mixture obtained in Example 2 was replaced with 0.24 mmol in terms of a zinc atom of diethylzinc, thereby obtaining 1.24 g of a polymer.

This polymer was dissolved in deuterated orthodichlorobenzene, and the solution was subjected to measurement by $^{13}$C-NMR. From a signal of $^{13}$C-NMR obtained, the terminal carbon and the amount of branches were measured. It was found that the ethyl branch and the propyl branch per 1000 carbons were below detectable limit.

INDUSTRIAL APPLICABILITY

The novel organometallic compound of the present invention is useful as a chain transfer agent in polymerization reaction of a double-bond containing compound, and can be used particularly as a reversible chain transfer agent in polymerization reaction, and is capable of producing a polymer having a carbon-metal bond at both terminals.

The invention claimed is:

1. An organometallic compound (1) represented by the following general formula (1)

[Chem. 1]

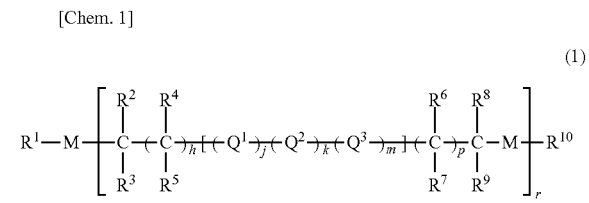

(1)

(in the general formula (1), M is a magnesium atom, a zinc atom, an Al—$R^{11}$ group, or a Ga—$R^{11}$ group, provided that $R^{11}$ is a hydrogen atom, a hydrocarbon group, a halogen atom, a silicon-containing group, or an oxygen-containing group; $R^1$ and $R^{10}$ are each independently a hydrocarbon group having 1 to 20 carbon atoms, or $R^1$ and $R^{10}$ may be united with each other to form a divalent connecting group ($R^{101}$) having 4 or more carbon atoms and optionally containing a heteroatom excluding carbon and hydrogen and thus form a ring; $R^2$ to $R^9$ are each independently a hydrogen atom, or a hydrocarbon group having 1 to 20 carbon atoms; $Q^1$ and $Q^3$ are each independently a divalent hydrocarbon group; $Q^2$ is a divalent connecting group containing a linkage by a heteroatom excluding carbon; h, j, k, m, and p are each independently 0 or 1; n is an integer of 0 to 10; and r is an integer of 2 to 10000, provided that:

$R^1$ to $R^{11}$ may be a group formed by substituting a part of the hydrogen atoms of the hydrocarbon group with a substituent containing a heteroatom excluding carbon and hydrogen; $Q^1$ and $Q^3$ may be a group formed by substituting a part of the hydrogen atoms of the divalent hydrocarbon group with a substituent containing a heteroatom excluding carbon and hydrogen;

when h is 0, at least one of $R^2$ and $R^3$ is a hydrocarbon group having 2 to 20 carbon atoms; when h is 1, at least one of $R^4$ and $R^5$ is a hydrocarbon group having 1 to 20 carbon atoms; when p is 0, at least one of $R^8$ and $R^9$ is a hydrocarbon group having 2 to 20 carbon atoms; when p is 1, at least one of $R^6$ and $R^7$ is a hydrocarbon group having 1 to 20 carbon atoms;

when n is 2 or more, plural $Q^1$, $Q^2$, $Q^3$, j, k, and m may be individually the same as or different from one another;

plural M may be the same as or different from one another; when plural $R^{11}$ are present, they may be the same as or different from one another; and plural $Q^1$, $Q^2$, $Q^3$, h, j, k, m, n, p, and $R^2$ to $R^9$ may be individually the same as or different from one another.

2. The organometallic compound (1) according to claim 1, which is represented by the following general formula (2), (3a), (3b), (3c), or (4).

[Chem. 2]

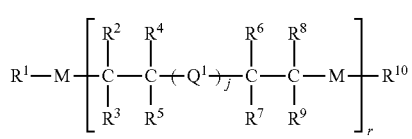
(2)

[Chem. 3]

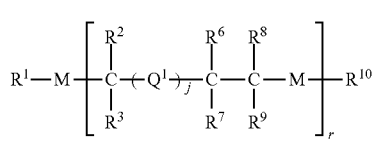
(3a)

[Chem. 4]

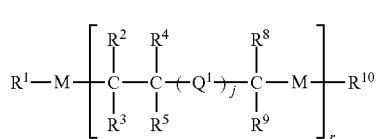
(3b)

[Chem. 5]

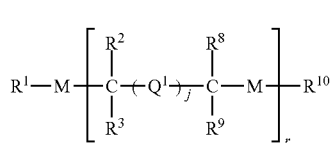
(3c)

[Chem. 6]

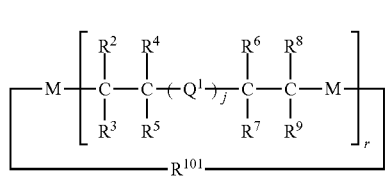
(4)

(in the general formulae (2), (3a), (3b), (3c), and (4), M, $R^1$ to $R^{10}$, $Q^1$, j, and r are each defined in the same way as in the general formula (1) of claim 1; and $R^{101}$ is a divalent connecting group having 4 or more carbon atoms and optionally containing a heteroatom excluding carbon and hydrogen).

3. The organometallic compound (I) according to claim 1 or 2, wherein M is an Al—$R^1$ group or a zinc atom.

4. An organometallic compound (5) represented by the following general formula (5)

[Chem. 7]

(5)

(in the general formula (5), A is a unit derived from a linear or branched α-olefin having 2 to 30 carbon atoms, a cyclic olefin, a diene, a polyene, or an aromatic vinyl compound; x, y, z, and w are each an integer of 1 or more; and x+y+z+w=8 to 100000;

M is a magnesium atom, a zinc atom, an Al—$R^{11}$ group, or a Ga—$R^{11}$ group, provided that $R^{11}$ is a hydrogen atom, a hydrocarbon group, a halogen atom, a silicon-containing group, or an oxygen-containing group; $R^1$ and $R^{10}$ are each independently a hydrocarbon group having 1 to 20 carbon atoms, or $R^1$ and $R^{10}$ may be united with each other to form a divalent connecting group ($R^{101}$) having 4 or more carbon atoms and optionally containing a heteroatom excluding carbon and hydrogen and thus form a ring; $R^2$ to $R^9$ are each independently a hydrogen atom, or a hydrocarbon group having 1 to 20 carbon atoms; $Q^1$ and $Q^3$ are each independently a divalent hydrocarbon group; $Q^2$ is a divalent connecting group containing a linkage by a heteroatom excluding carbon; h, j, k, m, and p are each independently 0 or 1; n is an integer of 0 to 10; and r is an integer of 0 to 10000, provided that:

$R^1$ to $R^{11}$ may be a group formed by substituting a part of the hydrogen atoms of the hydrocarbon group with a substituent containing a heteroatom excluding carbon and hydrogen; $Q^1$ and $Q^3$ may be a group formed by substituting a part of the hydrogen atoms of the divalent hydrocarbon group with a substituent containing a heteroatom excluding carbon and hydrogen;

when h is 0, at least one of $R^2$ and $R^3$ is a hydrocarbon group having 2 to 20 carbon atoms; when h is 1, at least one of $R^4$ and $R^5$ is a hydrocarbon group having 1 to 20 carbon atoms; when p is 0, at least one of $R^8$ and $R^9$ is a hydrocarbon group having 2 to 20 carbon atoms; when p is 1, at least one of $R^6$ and $R^7$ is a hydrocarbon group having 1 to 20 carbon atoms;

when n is 2 or more, plural $Q^1$, $Q^2$, $Q^3$, j, k, and m may be individually the same as or different from one another;

when r is 0, $R^1$ and $R^{10}$ are united with each other to form a divalent connecting group ($R^{101}$) having 4 or more carbon atoms and optionally containing a heteroatom excluding carbon and hydrogen and thus form a ring;

when r is 1 or more, plural M may be the same as or different from one another; when plural $R^{11}$ are present, they may be the same as or different from one another; and when r is 2 or more, plural $Q^1$, $Q^2$, $Q^3$, h, j, k, m, n, p, and $R^2$ to $R^9$ may be individually the same as or different from one another).

5. A method for producing the organometallic compound according to claim 1, comprising reacting in the presence of a transition metal compound (A) represented by the following general formula (A), a diene compound (B) represented by the following general formula (B) with an organometallic compound (C) represented by the following general formula (C)

[Chem. 8]

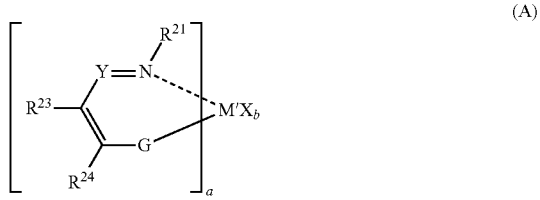

(A)

(in the general formula (A), M' is a transition metal atom selected from Groups 3 to 11 of the periodic table of the elements (Group 3 includes a lanthanoid and an actinoid); a is an integer of 1 to 3, which is the number of ligands coordinated with the transition metal atom M'; X is an atom or a group selected from the group consisting of a hydrogen atom, a halogen atom, an oxygen atom, a hydrocarbon group, a silicon-containing group, germanium-containing group, a tin-containing group, a boron-containing group, an aluminum-containing group, a phosphorus-containing group, an oxygen-containing group, a sulfur-containing group, a nitrogen-containing group, a halogen-containing group, and a hetrocyclic compound residue; b is an integer of 0 to 3, which is the number of X; when b is 2 or 3, X may be the same as or different from one another, and plural X may be united with one another to form a ring; Y is a nitrogen atom, or a carbon atom having a substituent $R^{22}$; G is an oxygen atom, a sulfur atom, a selenium atom, or a nitrogen atom having a substituent $R^{25}$; $R^{21}$ to $R^{25}$ may be the same as or different from one another, and are an atom or a group selected from the group consisting of a hydrocarbon group, a halogen atom, a hydrogen atom, a hydrocarbon-substituted silyl group, an oxygen-containing group, a nitrogen-containing group, a sulfur-containing group, a boron-containing group, an aluminum-containing group, a phosphorus-containing group, a halogen-containing group, a heterocyclic compound residue, a silicon-containing group, a germanium-containing group, and a tin-containing group; two or more of $R^{22}$ to $R^{25}$ may be united with one another to form a ring; and when a is 2 or 3, $R^{21}$s, $R^{22}$s, $R^{23}$s, $R^{24}$s, and $R^{25}$s may be individually the same as or different from one another, and one group of $R^{22}$-$R^{25}$ contained in any one of the ligands and one group of $R^{22}$-$R^{25}$ contained in another ligand may be united).

[Chem. 9]

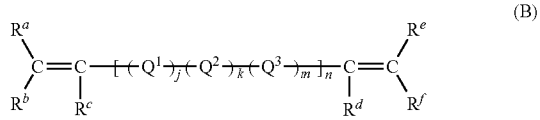

(B)

(in the general formula (B), $R^a$ to $R^f$ are each independently a hydrogen atom, or a hydrocarbon group having 1 to 20 carbon atoms, and may be a group formed by substituting a part of the hydrogen atoms of the hydrocarbon group with a substituent containing a heteroatom excluding carbon and hydrogen; and $Q^1$, $Q^2$, $Q^3$, j, k, m, and n are each defined in the same manner as in the general formula (1))

[Chem. 10]

R-M-R    (C)

(in the general formula (C), M is defined in the same manner as in the general formula (1); two R are each independently a hydrocarbon group having 1 to 20 carbon atoms, and may be a group formed by substituting a part of the hydrogen atoms of the hydrocarbon group with a substituent containing a heteroatom excluding carbon and hydrogen).

6. The method for producing the organometallic compound according to claim 5, wherein the transition metal compound (A) is a transition metal compound (A1) represented by the following general formula (A1)

[Chem. 11]

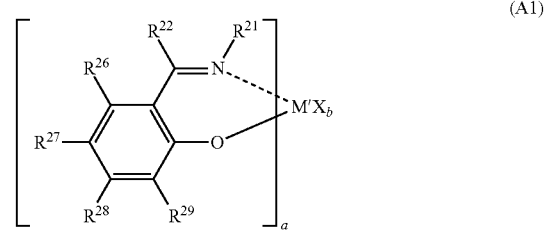

(A1)

(in the general formula (A1), M', a, X, b, $R^{21}$, and $R^{22}$ are each defined in the same manner as in the general formula (A) of claim 1; $R^{26}$ to $R^{29}$ may be the same as or different from one another, and are an atom or a group selected from the group consisting of a hydrogen atom, a hydrocarbon group, a halogen atom, a hydrocarbon-substituted silyl group, an oxygen-containing group, a nitrogen-containing group, a sulfur-containing group, a boron-containing group, an aluminum-containing group, a phosphorus-containing group, a halogen-containing group, a heterocyclic compound residue, a silicon-containing group, a germanium-containing group, and a tin-containing group, and of these, two or more may be united with one another to form a ring; and when a is 2 or 3, $R^{21}$s, $R^{22}$s, $R^{26}$s, $R^{27}$s, $R^{28}$s and $R^{29}$s may be individually the same as or different from one another, and one group of $R^{22}$ and $R^{26}$-$R^{29}$ contained in any one of the ligands and one group of $R^{22}$ and $R^{26}$-$R^{29}$ contained in another ligand may be united).

7. The method for producing the organometallic compound according to claim 5, wherein M is an Al—$R^{11}$ group, or a zinc atom.

8. The method for producing the organometallic compound according to any one of claims 5 to 7, which employs a co-catalyst and a carrier.

9. A method for producing an organometallic compound (5) represented by the following general formula (5), comprising reacting the organometallic compound (I) according to claim 1 with a linear or branched α-olefin having 2 to 30 carbon atoms, a cyclic olefin, a diene, or a polyene, or an aromatic vinyl compound

[Chem. 12]

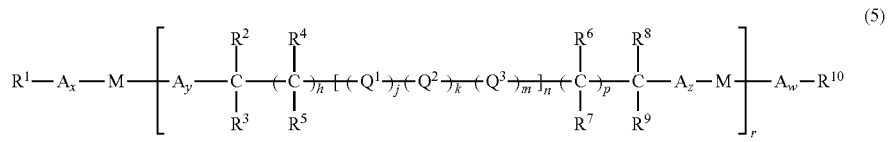

(5)

(in the general formula (5), A is a unit derived from a linear or branched α-olefin having 2 to 30 carbon atoms, a cyclic olefin, a dienes, a polyene, or an aromatic vinyl compound; x, y, z, and w are each an integer of 1 or more; x+y+z+w=8 to 100000;

M is a magnesium atom, a zinc atom, an Al—$R^{11}$ group, or a Ga—$R^{11}$ group, provided that $R^{11}$ is a hydrogen atom, a hydrocarbon group, a halogen atom, a silicon-containing group, or an oxygen-containing group; $R^1$ and $R^{10}$ are each independently a hydrocarbon group having 1 to 20 carbon atoms, or $R^1$ and $R^{10}$ may be united with each other to form a divalent connecting group ($R^{101}$) having 4 or more carbon atoms and optionally containing a heteroatom excluding carbon and hydrogen and thus form a ring; $R^2$ to $R^9$ are each independently a hydrogen atom, or a hydrocarbon group having 1 to 20 carbon atoms; $Q^1$ and $Q^3$ are each independently a divalent hydrocarbon group; $Q^2$ is a divalent connecting group containing a linkage by a heteroatom excluding carbon; h, j, k, m, and p are each independently 0 or 1; n is an integer of 0 to 10; and r is an integer of 0 to 10000, provided that:

$R^1$ to $R^{11}$ may be a group formed by substituting a part of the hydrogen atoms of the hydrocarbon group with a substituent containing a heteroatom excluding carbon and hydrogen; $Q^1$ and $Q^3$ may be a group formed by substituting a part of the hydrogen atoms of the divalent hydrocarbon group with a substituent containing a heteroatom excluding carbon and hydrogen;

when h is 0, at least one of $R^2$ and $R^3$ is a hydrocarbon group having 2 to 20 carbon atoms; when h is 1, at least one of $R^4$ and $R^5$ is a hydrocarbon group having 1 to 20 carbon atoms; when p is 0, at least one of $R^8$ and $R^9$ is a hydrocarbon group having 2 to 20 carbon atoms; when p is 1, at least one of $R^6$ and $R^7$ is a hydrocarbon group having 1 to 20 carbon atoms;

when n is 2 or more, plural $Q^1$, $Q^2$, $Q^3$, j, k, and m may be individually the same as or different from one another;

when r is 0, $R^1$ and $R^{10}$ are united with each other to form a divalent connecting group ($R^{101}$) having 4 or more carbon atoms and optionally containing a heteroatom excluding carbon and hydrogen and thus form a ring;

when r is 1 or more, plural M may be the same as or different from one another; when plural $R^{11}$ are present, they may be the same as or different from one another; and when r is 2 or more, plural $Q^1$, $Q^2$, $Q^3$, h, j, k, m, n, p, and $R^2$ to $R^9$ may be individually the same as or different from one another).

10. A method for producing a both-terminal-functional polymer comprising performing functional group conversion reaction at carbon-metal bonds of the organometallic compound (5) according to claim 4.

* * * * *